(12) United States Patent
Graham et al.

(10) Patent No.: US 6,730,507 B1
(45) Date of Patent: May 4, 2004

(54) USE OF HELPER-DEPENDENT ADENOVIRAL VECTORS OF ALTERNATIVE SEROTYPES PERMITS REPEAT VECTOR ADMINISTRATION

(75) Inventors: Frank L. Graham, Hamilton (CA); Robin Parks, Hamilton (CA)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/286,874

(22) Filed: Apr. 6, 1999

Related U.S. Application Data

(63) Continuation-in-part of application No. 09/251,955, filed on Feb. 17, 1999, now abandoned, which is a continuation-in-part of application No. 08/473,168, filed on Jun. 7, 1995, now Pat. No. 5,919,676, which is a continuation-in-part of application No. 08/250,885, filed on May 31, 1994, now Pat. No. 6,140,087, which is a continuation-in-part of application No. 08/080,727, filed on Jun. 24, 1993, now abandoned, and a continuation-in-part of application No. 08/719,217, filed on Sep. 25, 1996, now Pat. No. 6,080,569, which is a continuation-in-part of application No. 08/473,168, which is a continuation-in-part of application No. 08/250,885, which is a continuation-in-part of application No. 08/080,727.

(51) Int. Cl.$^7$ .............................. C12N 5/10; C12N 7/01; C12N 15/861

(52) U.S. Cl. ............................... 435/235.1; 435/320.1; 435/325; 435/366; 435/369

(58) Field of Search ...................... 435/320.1; 424/93.2

(56) References Cited

U.S. PATENT DOCUMENTS

| | | | |
|---|---|---|---|
| 4,510,245 | A | 4/1985 | Cousens et al. |
| 4,797,368 | A | 1/1989 | Carter et al. |
| 4,920,209 | A | 4/1990 | Davis et al. |
| 4,920,211 | A | 4/1990 | Tibbetts et al. |
| 5,670,488 | A | 9/1997 | Gregory et al. |
| 5,882,877 | A | 3/1999 | Gregory et al. |

FOREIGN PATENT DOCUMENTS

| | | |
|---|---|---|
| WO | WO 93/06223 | 4/1993 |
| WO | WO 93/19092 | 9/1993 |
| WO | WO 93/19191 | 9/1993 |
| WO | WO 94/08026 | 4/1994 |
| WO | WO 94/12649 | 6/1994 |
| WO | WO 95/27071 | 10/1995 |
| WO | WO 96/40955 | 12/1996 |
| WO | WO/97/25446 | 7/1997 |
| WO | WO 97/32481 | 9/1997 |
| WO | WO 98/13510 | 4/1998 |

OTHER PUBLICATIONS

Mack et al., "Circumvention of anti-adenovirus neutralizing immunity by administration of an adenoviral vector of an alternate serotype", Hum. Gene Ther., 8:99–109, Jan. 1997.*
Bailey et al., "Phylogenetic relationships among adenovirus serotypes", Virol., 205:438–452, 1994.*
Hay, "Origin of adenovirus DNA replication: role of the nuclear factor I binding site in vivo", J. Mol. Biol., 186:129–136, 1985.*
Temperley et al., "Identification of two distinct regions within the adenovirus minimal origin of replication that are required for adenovirus type 4 DNA replication in vitro", J. Virol., 65(9):5037–5044, Sep. 1991.*
Thorner et al., "Characterization of two divergent adenovirus 31 strains", Arch. Virol., 133:397–405, 1993.*
Klimkait et al., "EiB functions of type C adenoviruses play a role in the complementation of blocked adenovirus type 12 DNA replication and late gene transcription in hamster cells", Virol., 161:109–120, 1987.*
Hearing et al., "Identification of a repeated sequence element required for efficient encapsidation fo the adenovirus type 5 chromosome", J. Virol., 61(8):2555–2558, Aug. 1987.*
Anderson; Human gene therapy, 1998, Nature , vol. 392: 25–30.*
Verman et. al.; Gene therapy– promises, problems and prospects, 1997, Nature, vol. 389:239–242.*
Curiel; Strategies to Adapt Adenoviral Vectors for Targeted Delivery, 1980, Gene Therapy Strategies: 158–171.*
Navarro et. al.; Gene Therapy for Cancer, 1999, European Journal of cancer vol. 35, No. 6:867–885.*
Wilson et. al.; Immunomodulation to enhance gene therapy, 1995, Nature Medicine, vol. 1, No. 9: 887–889.*
Parks, R.J. et al. "Use of Helper-Dependent Adenoviral Vectors of Alternative Serotypes Permits Repeat Vector Administration" Gene Therapy. (1999) 1565–1573: 6(9), UK.
Morral, N. et al. "Administration of Helper-Dependent Adenoviral Vectors and Sequential Delivery of Different Vector Serotype for Long-Term Liver-Directed Gene Transfer in Baboons" Proceedings of the National Academy of Sciences,. 12816–12821: 96(22), USA.
Masreangeli, A., et al. "'Sero- Switch'Adenovirus- Mediated In Vivo Gene Trasnfer: Circumvention of Anti-Adenovirus Humoral Immune Defenses Against Repeat Adenovirus Vector Administration by Changing the Adenovirus Serotype" Human Gene Therapy, Jan. 1, 1996, 79–87, vol. 7, USA.
Russ, Andreas P. et al., 1996. Self-Deleting Retrovirus Vectors for Gene Therapy. J. of Virology, pp. 4927–4932.

(List continued on next page.)

Primary Examiner—Deborah J. Reynolds
Assistant Examiner—Joseph Woitach
(74) Attorney, Agent, or Firm—Joseph Fischer; Beusse Brownlee; Wolter Mora & Maire

(57) ABSTRACT

This invention responds to a long felt need, by providing in one embodiment, a helper virus based on the Ad2 serotype for use in the Cre/loxP system for the generation of Ad vectors deleted of all Ad protein coding sequences. Using this and helper virus based on Ad5, genetically identical hdAd that differ only in the virion protein components, which are derived from the helper virus, were produced. The vectors have identical expression characteristics in vitro, regardless of the serotype, and the sequential use of hdAd of different serotypes allows for successful repeat vector administration in vivo.

6 Claims, 9 Drawing Sheets

OTHER PUBLICATIONS

Anton, M., and F.L. Graham, 1995, Site–specific recombination mediated by an adenovirus vector expressing the Cre recombinase protein: a molecular switch for control of gene expression, J. Virol. 69:4600–4606.

Araki, K., J. Araki, J. I. Miyazski, and P. Vassali, 1995, Site–specific recombination of a transgene in fertilized eggs by transient expression of Cre recombinase. Proc. Nat'l Acad. Sci. USA 92: 160–164.

Bett, A. J., L. Prevec, and F. L. Graham, 1993, Packaging capacity and stability of human adenovirus type 5 vectors. J. Virol. 67:5911–5921.

Bett, A. J., W. Haddara, L. Prev, and F. L. Graham, 1994, An efficient and flexible system for construction of adenovirus vectors with insertions or deletions in early region 1 and 3. Proc. Nat'l Acad. Sci. USA 91: 8802–8806.

Di Santo, J. P., W. Mueller, D. Guy–Grand, A. Fischer, and K. Rajewsky, 1995, Lymphoid development in mice with a targeted deletion of the interleukin 2 receptor chain, Proc. Nat'l Acad. Sci. USA 92: 377–381.

Gage, P. J., B. Sauer, M. Levin and J. C. Glorioso. 1992. A cell–free recombination system for site–specific integration of multigenic shittle plasmids into the herpes simplex virus type 1 genome. J. Virol. 66: 5509–5515.

Graham, F. L. and L. Prevec. 1991. Manipulation of adenovirus vectors. In Murray E. J. (ed.), Methods in Molecular Biology. The Human Press Inc. Clifton, N. J. vol. 7 (Gene Transfer Protocols): 109–128.

Graham, F. L. and L. Prevec. 1992. Adenovirus–based expression vectors and recombinant vaccines. in: Vaccines: New Approaches in Immunological Problems., ed. Ellis, R. W. Butterworth–Heinemann Boston, MA: 363–390.

Graham, F. L., J. Smiley, W.C. Russel and R. Naim. 1977. Characteristics of a human cell line transformed by DNA from human adenovirus type 5., J. Gen. Virol. 36:59–72.

Gu, H., J.D. Marth, P.C. Orban, H. Mossmann and K. Rajewsky. 1994. Deletion of a DNA polymerase B gene segement in T cells using cell type–specific gene targeting. Science 265: 103–106.

Kilby, N.J., M. R. Snaith, and J. A. H. Murray. 1993. Site–specific recombinases: tools for genome engineering. Trends Genet. 9: 413–421.

Metzger, D., J. Clifford, H. Chiba and P. Chambon. 1995. Conditional site–specific recombination in mammalian cells using a ligand–dependent chimeric Cre protein. Proc. Nat'l Acad. Sci. USA 92: 6991–6995.

Pichel, J. G., Lasko, and H. Westphal. 1993. Timing of SV40 oncogene activation by site–specific recombination determines subsequent tumor progression during murine lens development. Oncogene 8: 3333–3342.

Sauer, B. 1994. Site–Specific recombination: developments and applications. Cur. Opin. Biotech. 5: 521–527.

Sauer, B., and N. Henderson. 1990. Targeted insertion of exogenous DNA into the eukaryotic genome by the Cre recombinase. The New Biologist 2: 441–449.

Sauer B., M Whealy, A. Robbins and L. Enquist. 1987. Site–specific insertion of DNA into pseudorabies virus vector. Proc. Nat'l. Acad. Sci. USA 84: 9108–9112.

Smith, A. J. H., M. A. DeSousa, B. Kwabbi–Addo, A. Heppell–Parton, H. Impey, and P. Rabbits. 1995. A site–directed chromosomal translocation induced in embryonic stem cells by Cre–loxP recombiantion. Nature Genetics 9: 376–385.

Sternberg, N., B. Sauer, R. Hoess, and K. Abremski. 1986. Bacteriophase P1 cre gene and its regulatory region; Evidence for multiple promotors and for regulation by DNA methylation., J. Mol. Biol. 187: 197–212.

Van Deursen, J., M. Fornerod, B. Van Rees, and G. Grosveld. 1995. Cre–mediated site specific translocation between non–homologous mouse chromosomes. Proc. Nat'l. Acad. Sci. USA 92: 7376–7380.

Mittal, S. K., McDermott, M.R., Johnson, D.C. Prevec, L. and F. L. Graham. 1993. Monitoring foreign gene expression by a human adenovirus–based vector using the firefly luciferase gene as a reporter, Virus Research, 28:67–90.

Hanke, T., Frank L. Graham, Kenneth L. Rosenthal and David C. Johnson. 1991. Identification of an immunodominant cytotoxic t–lymphocyte recognition site in glycoprotein B of herpes simplex virus by using recombinant adenovirus vectors and synthetic peptides. 1991. J. of Virology, 65: 1177–1186.

Graham, F. L., 1987. Growth of 293 cells in suspension culture. J. Gen. Virol. 68: 937–940.

Quantin, B., Leslie D. Pericaudet, Shahragim Tajbakhsh and Jean–Louis Mendel. 1992. Adenovirus as an expression vector in muscle cells in vivo. Proc. Nat'l. Acad. Sci. USA 89:2581–2584.

Rosenfeld, M. A. et al., 1992. In vivo transfer of the human cystic fibrosis transmembrane conductance regulator gene to the airway epithelium, Cell. 68: 143–155.

W.J. McGrory, D.S. Baulista and F.L. Graham. 1988. A simple technique for the reuse of early region 1 mutations into infectious human denovirus type 5, Virology 163: 614–617.

Wang, P., Anton, F. L. Graham and S. Bacchetti. High Frequency recombination between loxP sites in human chromosome mediated by an adenovirus vector expressing Cre recombinase. Submitted for Publication.

Sauer, Brian and Nancy Henderson. 1988. Site–specific DNA recombination in mammalian cells by the Cre recombinase of bacteriophage P1. Proc. Nat'l. Acad. Sci. USA 85: 5166–5170.

Gudrun Schiedner, et al., 1998. Genomic DNA transfer with a high–capacity adenovirus vector results in improved in vivo gene expression and decreased toxicity. Nature Genetics 18: 180–183.

Manal A. Morsy, et al., 1998. An adenoviral vector deleted for all viral coding sequences results in enhanced safety and extended expression of a leptin transgene. Proc. Nat'l. Acad. Sci. USA 95: 7866–7871.

Stephen Hardy, et al., 1997. Construction of Adenovirus Vectors through Cre–lox Recombination. Jour. Virol. 71: 3 1842–1849.

Parks, et al., 1996. A helper–dependent adenovirus vector system: Removal of helper virus by Cre–mediated excision of the viral packaging signal. Proc. Nat'l. Acad. Sci. USA 93: 13565–13570.

A. Kass–Eisler, L. Leinwand, J. Gall, B. Bloom and E. Falck–Pedersen. 1996. Cirumventing the immune response to adenovirus–mediated gene therapy. Gene Therapy 3: 154–162.

Roy, S., Shirley, P. S., McClelland, A. and Kaleko, M. 1998. Circumvention of Immunity to the Adenovirus Major Coat Protein Hexon. J. Viriology 72: (8) 6875–6879.

Mack, Charles A. et al. 1997. Circumvention of Anti–Adenovirus Neutralizing Immunity by Administration of an Adenoviral Vector of an Alternate Serotype. Hum. Gene Therapy 8: 99–109.

* cited by examiner

USE OF HELPER-DEPENDENT ADENOVIRAL VECTORS OF ALTERNATIVE SEROTYPES PERMITS REPEAT VECTOR ADMINISTRATION

CROSS-REFERENCES TO RELATED INVENTIONS

The application is a continuation-in-part of application Ser. No. 09/251,955, filed Feb. 17, 1999, abandoned, which was a continuation-in-part of application Ser. No. 08/473, 168, filed Jun. 7, 1995, now U.S. Pat. No. 5,919,676, which was a continuation-in-part of application Ser. No. 08/250, 885, filed May 31, 1994, now U.S. Pat. No. 6,140,087, which was a continuation-in-part of application Ser. No. 08/080,727, filed Jun. 24, 1993, abandoned. This application also is a continuation-in-part of application Ser. No. 08/719, 217, filed Sep. 25, 1996, now issued as U.S. Pat. No. 6,080,569, which is a continuation-in-part of application Ser. No. 08/473,168, filed Jun. 7, 1995, now U.S. Pat. No. 5,919,676, which is a continuation-in-part of application Ser. No. 08/250,885, filed May 31, 1994, now issued as U.S. Pat. No. 6,140,087, which is a continuation-in-part of application Ser. No. 08/08,727, filed Jun. 24, 1993, abandoned.

GOVERNMENT SUPPORT

Portions of the work described in this invention disclosure was supported by a grant from the US National Institutes of Health; accordingly, the U.S. Government may have certain rights in this invention.

BACKGROUND OF THE INVENTION

1. Field of the Invention

This invention relates to the field of gene therapy and vaccine delivery, and provides a significant advance in the art by facilitating repeat administration of a transgene in a vector, circumventing anti-vector immune responses, which diminish the efficacy of known gene delivery vectors.

2. Background of the Invention

Recently, adenovirus (Ads) vectors have received considerable attention for transgene delivery to mammalian cells generally and for gene therapy in particular due to several advantages over other vector systems, including high transduction efficiency of a variety of cell types comprised of both replicating and non-replicating cells, ease of growth, and relative safety (for review see Hitt et al. 1997). However, data from preclinical and clinical studies have shown that Ads also have several disadvantages, primarily due to the induction of both cellular and humoral immune responses to vector-derived antigens (Yang et al. 1994a, 1995a,b, 1996a,b, Dai et al. 1995, Gilgenkrantz et al. 1995, McCoy et al. 1995, Christ et al. 1997, Morral et al. 1997, van Ginkel et al. 1997, Kafri et al. 1998). Because of these immune responses, administration of first-generation Ad vectors (i.e. deleted of early region 1 (E1) or E1/E3) has generally resulted in only transient transgene expression and poor expression following repeat vector administration (Dong et al. 1996, Kaplan et al. 1996, St. George et al. 1996, Schulick et al. 1997). Reintroduction of the E3 region, which encodes functions involved in aiding virus escape from host immune responses, can prolong transgene expression in some animal models (Lee et al. 1995, Poller et al. 1996, Bruder et al. 1997, Ilan et al. 1997, Schowalter et al. 1997), and is reported to decrease the formation of anti-Ad neutralizing antibodies (Ilan et al. 1997). The use of second-generation Ad vectors, which are further deleted or attenuated in E2 or E4, can lead to decreased inflammatory responses and a longer duration of transgene expression (Engelhardt et al. 1994, Yang et al. 1994b, Goldman et al. 1995, Gao et al. 1996, Dedieu et al. 1997, Wang et al. 1997, Amalfitano et al. 1998), although not in all cases (Fang et al. 1996, Christ et al. 1997, Morral et al. 1997, Lusky et al. 1998). However induced antibody titers were similar to those generated against first generation vectors (Christ et al. 1997), thus compromising the ability to readminister the vector.

The development of systems for the generation of helper-dependent Ad vectors (hdAd) which are deleted for most if not all viral coding sequences (Mitani et al. 1995, Fisher et al. 1996, Haeker et al. 1996, Kochanek et al. 1996, Kumar-Singh and Chamberlain 1996, Lieber et al. 1996, Parks et al. 1996, Hardy et al. 1997, reviewed by Hitt et al. 1998), has allowed production of hdAd which can provide long term, high level transgene expression (Chen et al. 1997, Schiedner et al. 1998, Morsy et al. 1998), and which result in substantially reduced inflammatory and cellular immune responses (Morsy et al. 1998, Schiedner et al. 1998, Morral et al. 1998). However, as expected, deletion of all Ad coding sequences does not overcome the humoral immune response, and neutralizing antibodies are formed (J. L. Bramson, R. J. P. and F. L. G., unpublished results), thus reducing the effectiveness of hdAd vector readministration.

In an attempt to prevent vector-directed immune responses, many groups have explored the use of transient immune blockage at the time of Ad vector administration, or the induction of tolerance to Ad (Vilquin et al. 1995, Jooss et al. 1996, Kass-Eisler et al. 1996, Kolls et al. 1996, Lochmuller et al. 1996, Sawchuk et al. 1996, Smith et al. 1996, Yang et al. 1996c, Zepeda and Wilson 1996, Kaplan and Smith 1997, Kuzmin et al. 1997, Lieber et al. 1997, Scaria et al. 1997, Wolff et al. 1997, Zsengeller et al. 1997). These strategies have been somewhat successful, and allow repeat vector administration; however, complications and potential side-effects may make immune suppression impractical for clinical use. An alternative strategy to allow for repeat vector administration is the sequential use of different Ad serotypes. Neutralizing antibodies formed against one serotpe should have no effect on subsequent delivery of a different serotype, and this approach has allowed repeat administration of first generation Ad vectors (Kass-Eisler et al. 1996, Mastrangeli et al. 1996, Mack et al. 1997, Roy et al. 1998, A. L. Beaudet, unpublished results). Over 40 different serotypes of human Ads have been isolated, suggesting that, in theory, Ad vectors of different serotypes could be administered many times throughout the life of a patient. However, how to achieve this feat does not appear to have been disclosed or suggested for helper dependent vectors.

The Cre/loxP system for producing helper-dependent Ad vectors involves the use of a helper virus that contains a packaging signal flanked by loxP sites (Parks et al. 1996). Upon infection of a 293-derived cell line that stably expresses the bacteriophage P1 Cre recombinase (Chen et al. 1996), the packaging signal is excised from the helper virus DNA, rendering it unpackageable. The helper virus DNA retains the ability to replicate and provides all of the functions required in trans for the replication and packaging of a hdAd. This system facilitates the generation of high titer hdAd preparations with substantially reduced quantities of contaminating helper-virus. A key feature of the helper-dependent system is that the serotype of the hdAd is determined only by the helper virus. Therefore, in contrast to first generation vectors that require the construction of a new vector to switch serotypes, a series of genetically identical hdAds of different serotypes could be generated simply by changing the serotype of the helper.

SUMMARY OF THE INVENTION

We have developed a new helper adenovirus (Ad) based on serotype 2, Ad2LC8cCARP, for use in a the Cre/loxP system (Parks et al. 1996, Proc. Natl. Acad. Sci. USA 93:13565–13570) to generate Ad vectors deleted of all protein coding sequences (helper-dependent Ad vectors (hdAd)). A comparison of Ad2LC8cCARP and our helper virus developed previously (based on serotype 5, Ad5LC8cluc) showed that the two helper viruses amplified hdAd with a similar efficiency, and resulted in a similar yield and purity after large scale preparation of vector. In vitro, the resulting hdAd2 had a similar transduction efficiency and expressed levels of transgene (β-gal) identical to those produced by hdAd5. An important feature of the helper-dependent system is that all virion components, except the virion DNA, derive from the helper virus. Consequently vectors produced with help from Ad2LC8cCARP were not neutralized by antibodies against Ad5, and vectors produced with Ad5 helper were resistant to neutralizing antibodies against Ad2. Analysis of transgene expression in vivo after transduction of mouse liver by intravenous injection of the Ad2-based hdAd showed that the vector could efficiently transduce hepatocytes, and produce high levels of a foreign transgene (human secreted alkaline phosphatase), similar to those expressed by the hdAd generated with the Ad5 helper virus. Mice immunized with hdAd2 produced Ad2-neutralizing antibodies, which did not cross-react with hdAd5. To determine if successful repeat Ad vector administration could be achieved by sequential use of alternative Ad serotypes, we injected mice with hdAd2 (hSEAP) followed three months later by a lacZ-expressing hdAd of either the same or different serotype. Administration of a vector of the same serotype resulted in a 30- to 100-fold reduction in transgene expression compared to naive animals. In contrast, no decrease in transgene expression was observed when the second vector was of a different serotype. These results suggest that effective vector readministration can be achieved by the sequential use of hdAds based on alternative serotypes.

Accordingly, this invention responds to a long felt need, this invention provides, in one embodiment, a helper virus based on the Ad2serotype for use in the Cre/loxP system for the generation of Ad vectors deleted of all Ad protein coding sequences. Using this and helper virus based on Ad5, genetically identical hdAd that differ only in the virion protein components, which are derived from the helper virus, were produced. The vectors have identical expression characteristics in vitro, regardless of the serotype, and the sequential use of hdAd of different serotypes allows for successful repeat vector administration in vivo.

Accordingly, it is one object of this invention to provide a helper-dependent adenovirus vector (hdAd) administration system whereby repeat administration of a gene of interest is facilitated by using hdAd wherein all protein present in said hdAd is derived from a helper virus, the serotype of which is switched in the production of a vector to be used in a repeat hdAd administration.

Another object of this invention is to provide a generally applicable strategy, not restricted to adenoviruses, whereby repeat administration of a gene is facilitated, such that high level gene expression occurs on each administration.

Another object of this invention is to provide a system whereby helper adenoviruses of different serotypes are used to generate a series of hdAd vectors against which humoral and cellular immune responses are minimized, while providing for repeat administration of genes of interest.

Other objects and advantages of this invention will become apparent from a review of the complete disclosure and the appended claims.

DETAILED DISCLOSURE OF THE PREFERRED EMBODIMENTS AND BEST MODE

Figure 1:
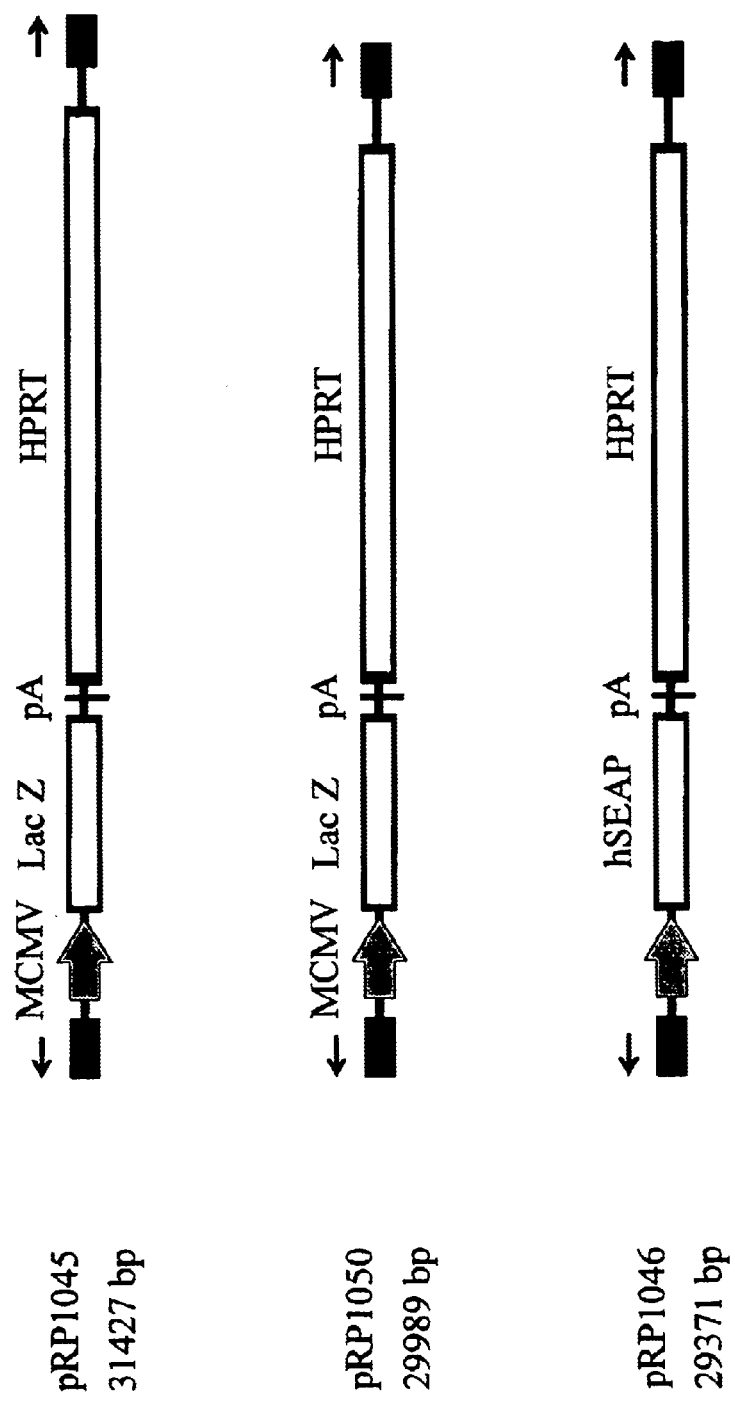
FIG. 1. pRP1045 (shown in linear form) is deleted of all Ad protein coding sequences but contains an Ad5 head-to-tail inverted terminal repeat (ITR) junction and packaging signal, and encodes the *E. coli* β-galactosidase gene under the regulation of the murine cytomegalovirus immediate-early promoter and Simian virus 40 polyadenylation sequence. pRP1045 also contains a ~22 kb Kent of the human hypoxanthine-guazine phosphoribosyltransferase (HPRT) gene as stuffer, in order to maintain the size of the resulting vector within the limits for efficient Ad DNA packaging (Parks and Graham 1997). pRP1050 is similar to pRP1045, but is deleted of a 1.2 kb StuI fragment from the HPRT sequence, and the resulting vectors (AdRP1045 and AdRP1050) have essentially identical expression characteristics. pRP1046 is similar in structure to pRP1050, but encodes a CDNA for human secreted alkaline phosphatase gene (hSEAP, Tropix) in place of the lacZ gene. The HPRT genomic sequence was obtained from Dr. Andrew J. Bett (Merck Research Laboratories, West Point, Pa.). All hdAd vectors were amplified using the appropriate helper virus in 293Cre4 cells, as previously described (Parks et al. 1996, Parks and Graham 1997), and the DNA structures of all hdAd vectors were confirmed by restriction digestion analysis of DNA isolated from virions. The titer of each vector was determined on 293 cells as the number of transducing particles, or blue forming units (BFU), per ml. For AdRP1046, the total particle count, as determined spectrophotometrically ($1A_{260}=1.1\times10^{12}$ particles per ml), was used to estimate the number of transducing particles, assuming a particle:transducing particle ratio of 100:1. For clarity, hdAd are designated with the appropriate serotype. For example, Ad5RP1050 and Ad2RP1050 are generated using Ad5LC8cluc and Ad2LC8cCARP, respectively.

The present invention provides a significant advance in the art of gene therapy and vaccine delivery, in that it provides a method whereby repeat administration of a gene vector according to this method can circumvent anti-vector immune responses. This is accomplished by modifying the protein coat of a viral gene vector on each repeat administration. While this may be accomplished using any helper-dependent viral system, the invention is exemplified with reference to helper-dependent adenoviruses. According to this embodiment of the invention, a helper-dependent adenovirus is produced encoding a gene, the expression of which is desired, either to induce a specific desired immune response against the encoded gene product, for vaccine applications, or because a particular genetic function is desired. For example, complementation of a genetic defect such as in cystic fibrosis, (e.g. provision of the CFTR gene product, see U.S. Pat. Nos. 5,882,877 and 5,670,488, hereby incorporated by reference), or provision of anti-sense RNA, or provision of an enzyme or enzyme inhibitor, or structural gene product or required hormone or cytokine or immunomodulatory protein, all may be accomplished according to the present methodology without inhibition by recipient's humoral or cellular immune responses elicited by a previous exposure to the gene vector.

In one exemplary application of the present invention, a desired gene of interest is cloned into a helper-dependent adenoviral vector (hdAd), comprising the left adenoviral ITR, the right adenoviral ITR, an adenoviral packaging signal, and sufficient additional sequences to ensure efficient packaging of the hdAd vector thus produced. The desired gene of interest is cloned into the hdAd vector with required transcriptional initiation (promoter) and termination signals, as are known in the art, in order to ensure efficient transcription and translation of the gene of interest, upon introduction into an appropriate host cell, by means of the adenoviral vector. The hdAd vector preferably has a genomic size between about 75% and 100% of the natural genome size of an adenovirus, to ensure efficient packaging of the adenoviral vector genome. The hdAd is co-transfected into an appropriate cell in vitro with the helper virus, to generate a stock of hdAd vector. Preferably, the cell provides functions necessary for replication or packaging of the hdAd vector, as in 293 cells which complement adenoviral vector deletions in the E1 coding sequences, or such complementation may be provided by the helper virus. In addition, it is preferred that an efficient method is provided for elimination of helper virus from the stock of hdAd vector that is produced. As disclosed in co-pending applications related to the present application, and in PCT publications WO96/40955, WO95/00655, and WO98/13510, all of which are hereby incorporated by reference for this purpose, a system may be employed whereby a helper virus having a packaging signal is flanked by lox sites. Co-transfection of such a virus into a cell in which the Cre recombinase is expressed results in excision of the helper virus packaging signal, making the genome of the helper virus non-packageable. Since the hdAd vector genome encoding the gene of interest has a packaging signal, the hdAd vector is efficiently packaged, essentially free of helper viral genome contamination. Additional methodologies may be employed to eliminate helper viral genome contamination, and those technologies are applicable to this invention, whether previously reported on, or when such technologies become publicly available. Thus, regardless of the methodology by which helper viral genome contamination is limited, an essentially pure preparation of hdAd vector is produced which contains a vector genome encoding a desired gene of interest. The capsid of the packaged hdAd vector is completely defined by structural proteins of the helper virus. Accordingly, by preparing a helper virus of a first adenoviral serotype, e.g. serotype 5, for packaging of a first hdAd vector preparation, and a subsequent helper virus from a second adenoviral serotype, e.g. human Ad serotype 2, serotype 1, serotype 6, or other human adenoviruses or adenoviruses derived from non-human serotypes, for packaging of a second hdAd vector preparation, and a subsequent helper virus from a third adenoviral serotype for packaging of a third hdAd vector preparation, and so forth, essentially unlimited variations in the capsid serotype may be produced, without the need to make any modifications to the hdAd vector genome. Accordingly, in one aspect of this invention, there is provided a kit comprising a series of helper adenoviruses of different serotypes, such that upon production of any given hdAd vector, a complete regimen of an essentially unlimited number of booster hdAd vector administrations may be initiated, without inhibition by anti-vector immune responses previously elicited in a recipient thereof. In addition, upon decay of immune responses directed against a first serotype, that same serotype may once again be used, thereby expanding the number of consecutive administrations of the vector that may be employed.

In reviewing the detailed disclosure which follows, it should be borne in mind that any publications referenced herein are hereby incorporated by reference in this application in order to more fully describe the state of the art to which the present invention pertains.

It is important to an understanding of the present invention to note that all technical and scientific terms used herein, unless otherwise defined, are intended to have the same meaning as commonly understood by one of ordinary skill in the art. The techniques employed herein are also those that are known to one of ordinary skill in the art, unless stated otherwise.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

The terms used herein are not intended to be limiting of the invention. For example, the term "gene" includes cDNAs, RNA, or other polynucleotides that encode gene products. "Foreign gene" denotes a gene that has been obtained from an organism or cell type other than the organism or cell type in which it is expressed; it also refers to a gene from the same organism that has been translocated from its normal situs in the genome. In using the terms "nucleic acid", "RNA", "DNA", etc., we do not mean to limit the chemical structures that can be used in particular steps. For example, it is well known to those skilled in the art that RNA can generally be substituted for DNA, and as such, the use of the term "DNA" should be read to include this substitution. In addition, it is known that a variety of nucleic acid analogues and derivatives is also within the scope of the present invention. "Expression" of a gene or nucleic acid encompasses not only cellular gene expression, but also the transcription and translation of nucleic acid(s) in cloning systems and in any other context. The term "recombinase" encompasses enzymes that induce, mediate or facilitate recombination, and other nucleic acid modifying enzymes that cause, mediate or facilitate the rearrangement of a nucleic acid sequence, or the excision or insertion of a first nucleic acid sequence from or into a second nucleic acid sequence. The "target site" of a recombinase is the nucleic acid sequence or region that is recognized (e.g., specifically binds to) and/or acted upon (excised, cut or induced to recombine) by the recombinase. The term "gene product" refers primarily to proteins and polypeptides encoded by other nucleic acids (e.g.; non-coding and regulatory RNAs such as tRNA, sRNPs). The term "regulation of expression" refers to events or molecules that increase or decrease the synthesis, degradation, availability or activity of a given gene product.

The present invention is also not limited to the use of the cell types and cell lines used herein. Cells from different tissues (breast epithelium, colon, lymphocytes, etc.) or different species (human, mouse, etc.) are also useful in the present invention.

It is important in this invention to detect the generation and expression of recombinant nucleic acids and their encoded gene products. The detection methods used herein include, for example, cloning and sequencing, ligation of oligonucleotides, use of the polymerase chain reaction and variations thereof (e.g., a PCR that uses 7-deaza GTP), use of single nucleotide primer-guided extension assays, hybridization techniques using target-specific oligonucleotides that can be shown to preferentially bind to complementary sequences under given stringency conditions, and sandwich hybridization methods.

Sequencing may be carried out with commercially available automated sequencers utilizing labeled primers or terminators, or using sequencing gel-based methods. Sequence analysis is also carried out by methods based on ligation of oligonucleotide sequences which anneal immediately adjacent to each other on a target DNA or RNA molecule (Wu and Wallace, *Genomics* 4: 560–569 (1989); Landren et al., *Proc. Natl. Acad. Sci.* 87: 8923–8927 (1990); Barany, F., *Proc. Natl. Acad. Sci.* 88: 189–193 (1991)). Ligase-mediated covalent attachment occurs only when the oligonucleotides are correctly base-paired. The Ligase Chain Reaction (LCR), which utilizes the thermostable Taq ligase for target amplification, is particularly useful for interrogating late onset diabetes mutation loci. The elevated reaction temperatures permits the ligation reaction to be conducted with high stringency (Barany, F., *PCR Methods and Applications* 1: 5–16 (1991)).

The hybridization reactions may be carried out in a filter-based format, in which the target nucleic acids are immobilized on nitrocellulose or nylon membranes and probed with oligonucleotide probes. Any of the known hybridization formats may be used, including Southern blots, slot blots, "reverse" dot blots, solution hybridization, solid support based sandwich hybridization, bead-based, silicon chip-based and microtiter well-based hybridization formats.

The detection oligonucleotide probes range in size between 10–1,000 bases. In order to obtain the required target discrimination using the detection oligonucleotide probes, the hybridization reactions are generally run between 20°–60° C., and most preferably between 30°–50° C. As known to those skilled in the art, optimal discrimination between perfect and mismatched duplexes is obtained by manipulating the temperature and/or salt concentrations or inclusion of formamide in the stringency washes.

The cloning and expression vectors described herein are introduced into cells or tissues by any one of a variety of known methods within the art. Such methods are described for example in Sambrook et al., *Molecular Cloning: A Laboratory Manual*, Cold Spring Harbor Laboratory, New York (1992), which is hereby incorporated by reference. See, also, Ausubel et al., *Current Protocols in Molecular Biology*, John Wiley and Sons, Baltimore, Md. (1989); Hitt et al, "Construction and propagation of human adenovirus vectors," in *Cell Biology: A Laboratory Handbook Ed.* J. E. Celis., Academic Press. $2^{nd}$ Edition, Volume 1, pp: 500–512, 1998; Hitt et al, "Techniques for human adenovirus vector construction and characterization," in *Methods in Molecular Genetics, Ed.* K. W. Adolph, Academic Press, Orlando, Fla., Volume 7B, pp:12–30, 1995; Hitt, et al., "Construction and propagation of human adenovirus vectors," in *Cell Biology: A Laboratory Handbook,"* Ed. *J. E. Celis. Academic Press.* pp:479–490, 1994, also hereby incorporated by reference.

The methods include, for example, stable or transient transfection, lipofection, electroporation and infection with recombinant viral vectors.

The protein products of recombined and unrecombined coding sequences may be analyzed using immune techniques. For example, a protein, or a fragment thereof is injected into a host animal along with an adjuvant so as to generate an immune response. Immunoglobulins which bind the recombinant fragment are harvested as an antiserum, and are optionally further purified by affinity chromatography or other means. Additionally, spleen cells may be harvested from an immunized mouse host and fused to myeloma cells to produce a bank of antibody-secreting hybridoma cells. The bank of hybridomas is screened for clones that secrete immunoglobulins which bind to the variant polypeptides but poorly or not at all to wild-type polypeptides are selected, either by pre-absorption with wild-type proteins or by screening of hybridoma cell lines for specific idiotypes that bind the variant, but not wild-type, polypeptides.

Nucleic acid sequences capable of ultimately expressing the desired variant polypeptides are formed from a variety of different polynucleotides (genomic or cDNA, RNA, synthetic olignucleotides, etc.) as well as by a variety of different techniques.

The DNA sequences are expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors contain selection markers (e.g., markers based on tetracycline resistance or hygromycin resistance) to permit detection and/or selection of those cells transformed with the desired DNA sequences. Further details can be found in U.S. Pat. No. 4,704,362.

Polynucleotides encoding a variant polypeptide include sequences that facilitate transcription (expression sequences) and translation of the coding sequences such that the encoded polypeptide product is produced. Construction of such polynucleotides is well known in the art. For example, such polynucleotides include a promoter, a transcription termination site (polyadenylation site in eukaryotic expression hosts), a ribosome binding site, and, optionally, an enhancer for use in eukaryotic expression hosts, and optionally, sequences necessary for replication of a vector.

E. Coli is one prokaryotic host useful particularly for cloning DNA sequences of the present invention. Other microbial hosts suitable for use include bacilli, such as Bacillus subtilus, and other enterobacteriaceae, such as Salmonella, Serratia, and various Pseudomonas species. Expression vectors are made in these prokaryotic hosts which will typically contain expression control sequences compatible with the host cell (e.g., an origin of replication). In addition, any number of a variety of well-known promoters are used, such as the lactose promoter system, a tryptophan (Trp) promoter system, a beta-lactamase promoter system, or a promoter system from phage lambda. The promoters typically control expression, optionally with an operator sequence, and have ribosome binding site sequences, for example, for initiating and completing transcription and translation.

Other microbes, such as yeast, are used for expression. Saccharomyces is a suitable host, with suitable vectors having expression control sequences, such a promoters, including 3-phosphoglycerate kinase or other glycolytic enzymes, and an origin of replication, termination sequences, etc. as desired.

In addition to microorganisms, mammalian tissue cell culture is used to express and produce the polypeptides of the present invention. Eukaryotic cells are preferred, because a number of suitable host cell lines capable of secreting intact human proteins have been developed in the art, and include the CHO cell lines, various COS cell lines, HeLa cells, myeloma cell lines, Jurkat cells, and so forth. Expression vectors for these cells include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobin genes, SV40, Adenovirus, Bovine Papilloma Virus, Herpes Virus, and so forth. The vectors containing the DNA segments of interest (e.g., polypeptides encoding a variant polypeptide) are transferred into the host cell by well-known methods, which vary depending on the type of cellular host. For example, calcium chloride transfection is commonly utilized for prokaryotic cells, whereas calcium phosphate treatment or electroporation is usefull for other cellular hosts.

The method lends itself readily to the formulation of test kits for use in diagnosis or kits for production of vectors for gene therapy or vaccination. Such a kit comprises a carrier compartmentalized to receive in close confinement one or more containers wherein a first container contains reagents useful in the localization of the labeled probes, such as enzyme substrates. Still other containers contain restriction enzymes, buffers etc., together with instructions for use.

Those skilled in the art will appreciate that for viral DNA replication and packaging of viral DNA into virion particles, only three regions of the viral DNA are known to be required in cis. These are the left inverted terminal repeat, or ITR, (bp 1 to approximately 103) the packaging signals (approximately 194 to 358 bp) (Hearing and Shenk, 1983, Cell 33: 695–703; Grable and Hearing 1992, J. Virol. 64: 2047–2056) and the right ITR. Among the regions of the viral genome that encode proteins that function in trans, two have been most important in the design and development of adenovirus vectors. These are early region 3 (E3) located between approximately 76 and 86 mu (mu=% distance from the left end of the conventionally oriented genome) and early region 1 (E1) located between approximately 1 and 11 mu E3 sequences have long been known to be nonessential for virus replication in cultured cells and many viral vectors have deletions of E3 sequences so that the capacity of the resulting vector backbone for insertion of foreign DNA is thereby increased significantly over that allowable by the wild-type virus (Bett, A. J., Prevec, L., and Graham, F. L. Packaging capacity and stability of human adenovirus type 5 vectors. J. Virol. 67: 5911–5921, 1993.). E1 encodes essential functions. However, E1 can also be deleted, providing that the resulting virus is propagated in host cells, such as the 293 cell line, PER-C6 cells, 911 cells, and the like, which contain and express E1 genes and can complement the deficiency of E1(-) viruses.

Viruses with foreign DNA inserted in place of E1 sequences, and optionally also carrying deletions of E3 sequences are conventionally known as "first generation" adenovirus vectors. First generation vectors are of proven utility for many applications. They can be used as research tools for high-efficiency transfer and expression of foreign genes in mammalian cells derived from many tissues and from many species. First generation vectors can be used in development of recombinant viral vaccines when the vectors contain and express antigens derived from pathogenic organisms. The vectors can be used for gene therapy, because of their ability to efficiently transfer and express foreign genes in vivo, and due to their ability to transduce both replicating and nonreplicating cells in many different tissues. Adenovirus vectors are widely used in these applications.

There are many known ways to construct adenovirus vectors. As discussed above, one of the most commonly employed methods is the so called "two plasmid" technique. In that procedure, two noninfectious bacterial plasmids are constructed with the following properties: each plasmid alone is incapable of generating infectious virus. However, in combination, the plasmids potentially can generate infectious virus, provided the viral sequences contained therein are homologously recombined to constitute a complete infectious virus DNA. According to that method, typically one plasmid is large (approximately 30,000–35,000 nt) and contains most of the viral genome, save for some DNA segment (such as that comprising the packaging signal, or encoding an essential gene) whose deletion renders the plasmid incapable of producing infectious virus. The second plasmid is typically smaller (e.g. 5000–10,000 nt), as small size aids in the manipulation of the plasmid DNA by recombinant DNA techniques. Said second plasmid contains viral DNA sequences that partially overlap with sequences present in the larger plasmid. Together with the viral sequences of the larger plasmid, the sequences of the second plasmid can potentially constitute an infectious viral DNA. Cotransfection of a host cell with the two plasmids produces an infectious virus as a result of homologous recombination between the overlapping viral DNA sequences common to the two plasmids. One particular system in general use by those skilled in the art is based on a series of large plasmids known as pBHG10, pBHG11 and pBHGE3 described by Bett, A. J., Haddara, W., Prevec, L. and Graham, F. L: "An efficient and flexible system for construction of adenovirus vectors with insertions or deletions in early regions 1 and 3," Proc. Natl. Acad. Sci. US 91: 8802–8806, 1994 and in U.S. patent application Ser. No. 08/250,885, now issued as U.S. Pat. No. 6,140,087, and published as WO95/00655 (hereby incorporated by reference). Those plasmids contain most of the viral genome and are capable of producing infectious virus but for the deletion of the packaging signal located at the left end of the wild-type viral genome. The second component of that system comprises a series of "shuttle" plasmids that contain the left approximately 340 nt of the Ad genome including the packaging signal, optionally a polycloning site, or optionally an expression cassette, followed by viral sequences from near the right end of E1 to approximately 15 mu or optionally to a point further rightward in the genome. The viral sequences rightward of E1 overlap with sequences in the pBHG plasmids and, via homologous recombination in cotransfected host cells, produce infectious virus. The resulting viruses contain the packaging signal derived from the shuttle plasmid, as well as any sequences, such as a foreign DNA inserted into the polycloning site or expression cassette located in the shuttle plasmid between the packaging signal and the overlap sequences. Because neither plasmid alone has the capability to produce replicating virus, infectious viral vector progeny can only arise as a result of recombination within the cotransfected host cell. Site-specific methods for achieving recombination may also be employed when practising the present invention.

It has been shown that use of hdAds can lead to prolonged transgene expression and reduced immune and inflammatory responses compared to first generation Ad vectors (Morral et al. 1988, Morsy et al. 1998, Scheidner et al. 1998). HdAds retain the other beneficial properties of Ad vectors, mainly virion stability during vector propagation and purification, and high transduction efficiency of replicating and quiescent cells, while eliminating some of the obstacles and concerns that have been raised with respect to first- and second-generation Ads.

The instant disclosure demonstrates that, should transgene expression levels decrease over time, the use of hdAds of alternative serotypes permits readministration of a vector with the identical genotype. It is important to note that, in our experiments, repeat administration was performed with a different reporter gene than was carried by the vector used in the initial animal immunization. Since vector persistence (and hence transgene expression) is influenced by immune responses to both vector and transgene (Dai et al. 1995, Dong et al. 1996, Tripathy et al. 1996, Christ et al. 1997, Michou et al. 1997, Morral et al. 1997), the effectiveness of vector readministration using hdAd's may ultimately depend primarily on the immunogenicity of the therapeutic gene. Accordingly, this disclosure demonstrates that, in the absence of transgene effects, the sequential use of hdAd of alternative serotype is an effective strategy for vector readministration. Accordingly, therapeutic genes encoding products of low immunogenicity may be repeatedly administered according to the instant disclosure. In addition, in vaccine applications, in which repeat administration of a gene encoding a particular gene product against which an immune response is desired, or when administration of a second, third, fourth etc. gene is desired, ability to overcome unwanted immune responses induced by a previous exposure to a vector is highly desirable.

Having generally described the present invention, the following specific examples provide additional written and illustrative description of the invention and the methods of practicing the invention, including the best mode thereof. However, those skilled in the art will appreciate that modifications and variations on the specifics of the invention as disclosed in these examples may be made, without departing from the essential features of this invention, which are defined by the appended claims, and the equivalents thereof.

EXAMPLE 1

Cell and Virus Culture

All cell culture media and reagents were obtained from Gibco Laboratories (Grand Island, N.Y.). 293 (Graham et al. 1977) and A549 (human lung carcinoma, ATCC CCL 185) cells were grown in monolayer in F-11 minimum essential medium supplemented with 100 U of penicillin per ml, 100 mg of streptomycin per ml, 2.5 mg fungizone per ml, and 10% fetal bovine serum for cell maintenance or 5% horse serum after virus infection. Recombinant Ad helper viruses were grown and titered on 293 cells, as previously described (Hitt et al. 1995). The 293-derived cell line that stably expresses the Cre recombinase, 293Cre4 (Chen et al. 1996), was propagated in complete F-11 medium supplemented with 0.4 mg/ml G418.

EXAMPLE 2

Helper-Dependent Adenovirus Vector Constructs

With reference to FIG. 1, pRP1045 (shown in linear form) is deleted of all Ad protein coding sequences but contains an Ad5 head-to-tail inverted terminal repeat (ITR) junction and packaging signal, and encodes the *E coli* β-galactosidase gene under the regulation of the murine cytomegalovirus immediately promoter and Simian virus 40 polyadenylation sequence. pRP1045 also contains a ~22 kb fragment of the human hypoxanthine-guanine phosphoribosyltransferase (HPRT) gene as stuffer, in order to maintain the size of the resulting vector within the limits for efficient Ad DNA packaging (Parks and Graham 1997). pRP1050is similar to pRP1045, but is deleted of a 1.2 kb StuI fragment from the HPRT sequence, and the resulting vectors (AdRP1045 and AdRP1050) have essentially identical expression characteristics. pRP1046 is similar in structure to pRPIO50, but encodes a cDNA for human secreted alkaline phosphatase gene (hSEAP, Tropix) in place of the lacZ gene. The HPRT genomic sequence was obtained from Dr. Andrew J. Bett (Merck Research Laboratories, West Point, Pa.). All hdAd vectors were amplified using the appropriate helper virus in 293Cre4 cells, as previously described (Parks et al. 1996, Parks and Graham 1997), and the DNA structures of all hdAd vectors were confirmed by restriction digestion analysis of DNA isolated from virions. The titer of each vector was determined on 293 cells as the number of transducing particles, or blue forming units (BFU), per ml. For AdRP1046, the total particle count, as determined spectrophotometrically ($1A_{260}=1.1 \times 10^{12}$ particles per ml), was used to estimate the number of transducing particles, assuming a particle:transducing particle ratio of 100:1. For clarity, hdAd are designated with the appropriate serotype. For example, Ad5RP1050 and Ad2RP1050 are generated using Ad5LC8cluc and Ad2LC8cCARP, respectively.

EXAMPLE 3

Production of Helper-Dependent Adenovirus Vectors

Helper-dependent Ad vectors were propagated and titered as previously described (Parks et al. 1996). pRP1045 is a hdAd deleted of all Ad protein coding sequences, but containing an Ad5 head-to-tail inverted terminal repeat (ITR) junction and packaging signal, as well as the *E. coli* b-galactosidase gene under the regulation of the murine cytomegalovirus immediate early promoter (MCMV) and Simian virus 40 polyadenylation (pA) sequence (FIG. 1). In order to maintain the size of the vector above the limit for efficient DNA packaging (~28 kb, Parks and Graham 1997), pRP1045 also contains a ~22 kb fragment of eukaryotic DNA derived from the human hypoxanthine-guanine phosphoribosyltransferase (HPRT) gene, as described elsewhere (Parks et al. submitted). pRP1050 is essentially identical to pRP1045, but is deleted of a 1.2 kb StuI fragment from the HPRT sequence, and has expression characteristics identical to pRP1045 (R. J. P. and F. L. G., unpublished results). pRP1046 is similar in structure to pRP1050, but contains the human secreted alkaline phosphatase cDNA (hSEAP, Tropix) replacing the lacZ gene. For clarity, hdAd will be designated with the appropriate serotype. For example, Ad5RP 1050and Ad2RP1050are generated using Ad5LC8cluc and Ad2LC8cCARP, respectively. For Ad2RP1046, the titer of the vector was determined spectrophotometrically, assuming $1A_{260}=1.1 \times 10^{12}$ particles.

EXAMPLE 4

Construction of a Cre/loxP Helper Virus based on Ad2

Figure 2A:
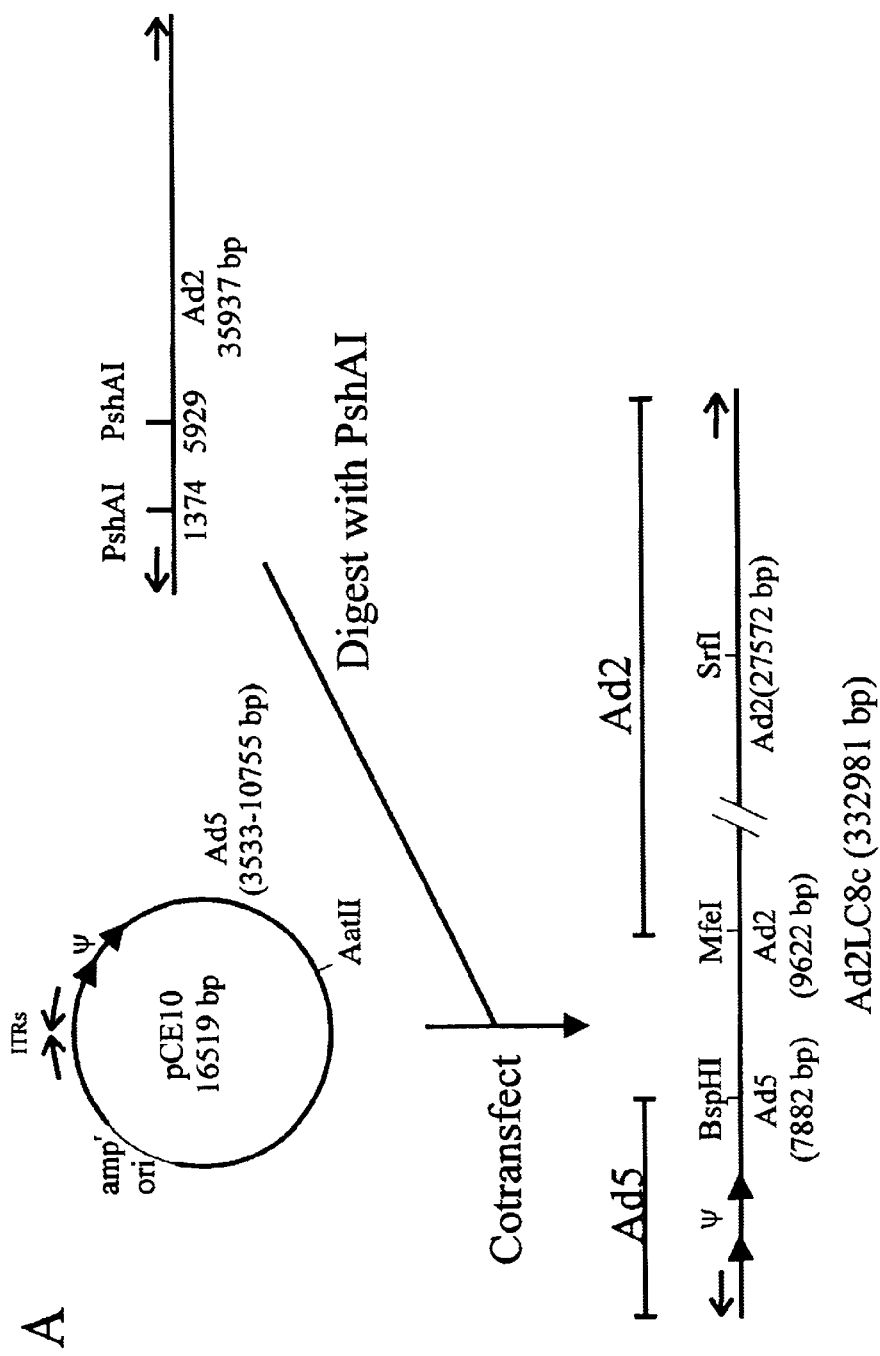
FIG. 2. Construction of Ad2LC8cCARP. Panel A: Strategy for the generation of an Ad2virus with a loxP-flanked packaging signal. Panel B: Strategy for the rescue of a stuffer segment into the E3 region of Ad2LC8c. Ad2LC8cCARP was constructed by a combination of molecular cloning and in vivo recombination techniques, as detailed in the Materials and Methods. The final viral construct, Ad2LC8cCARP, is deleted of Ad sequences between 339–3533 bp (E1), and contains a packaging signal flanked by loxP sites. Ad2LC8cCARP also contains a 5.6 kb fragment of lambda DNA inserted within the E3 region. Regions of the Ad genome are delineated by whether they are of Ad2or Ad5origin, and the appropriate nucleotide number according to the conventional Ad2or Ad5map. Restriction enzyme sites used in virus construction are also shown. Ad5packaging signal (Ψ), loxP sites (black triangles), Ad5ITR (black arrow).

The Ad2-based helper virus, Ad2LC8cCARP was constructed using both molecular cloning and in vivo genetic recombination techniques (FIG. 2A). pLC8c was used to provide the "left end" of the helper virus (i.e. left ITR and floxed packaging signal), and has been previously described (Parks et al. 1996). Initially, an AatII fragment was removed from pLC8c in order to reduce the Ad5 sequences contained within the plasmid. The resulting plasmid, pCE10, was cotransfected into 293 cells with Ad2 genomic DNA digested with PshAI. The resulting viruses were screened by restriction analysis for those which contained the majority of protein coding sequences derived from the Ad2 virus. One virus, designated Ad2LC8c, had resulted from a recombination event between an MfeI site located at 9622 bp of the conventional Ad2 map and a BspHI site located at 7882 bp of the Ad5 map. Thus, in Ad2LC8c all coding sequences for virion capsid proteins, with the exception of pIX, are derived from Ad2.

Figure 2B:
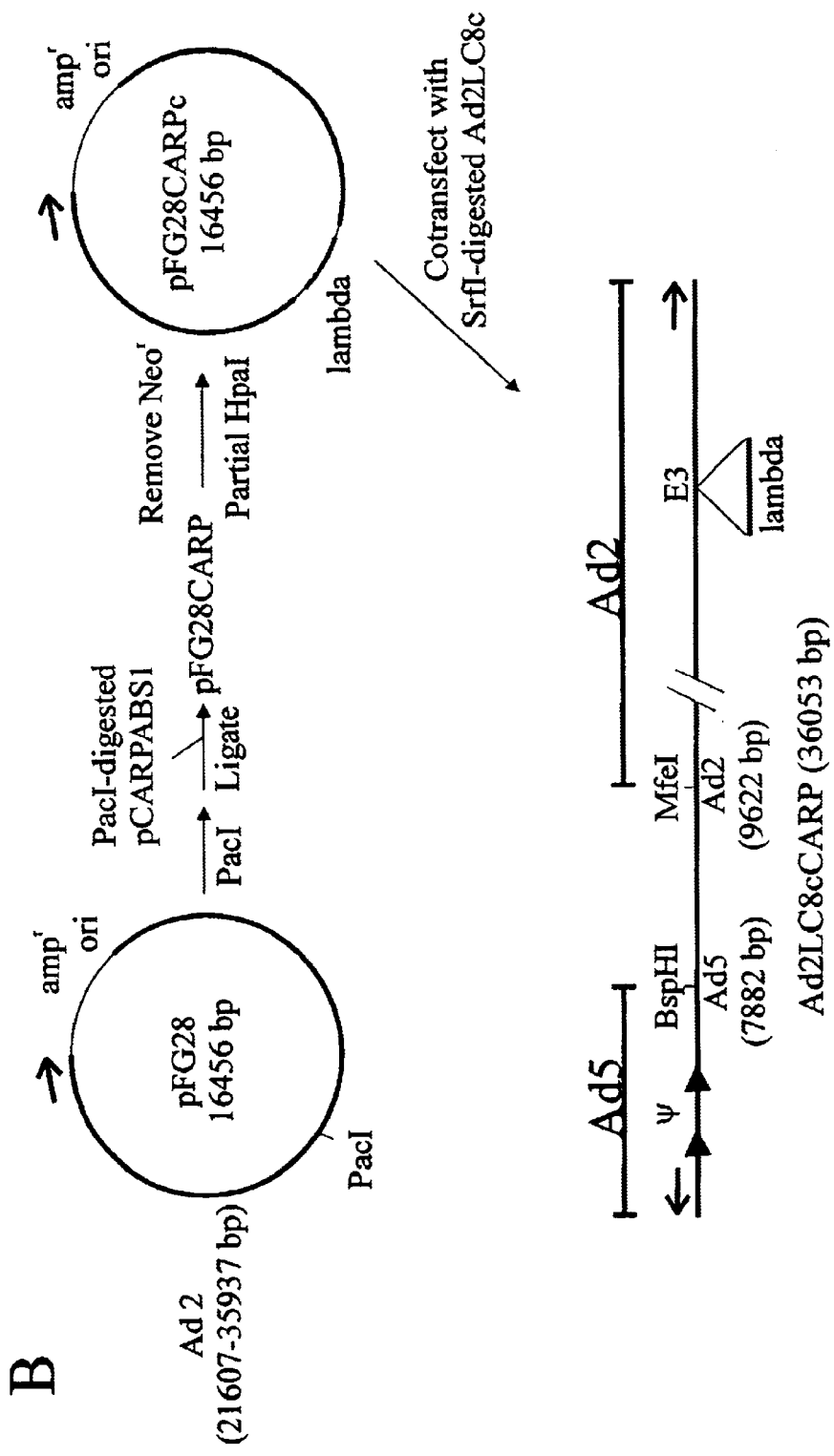

Because of the requirement for multiple serial passages in order to increase the titer of hdAd, the formation of replication competent adenovirus (RCA) is of concern. Once generated, RCA can rapidly outgrow the vector, leading to highly contaminated vector stocks. We have shown that the inclusion of a "stuffer" segment within the E3 region, such that recombination between the helper virus and the Ad5 sequences contained in the 293 or 293Cre cells results in a virus which is above the upper packaging limit for Ad virions (approximately 105% of the wild type genome, Bett et al. 1993), can eliminate the potential for RCA (Parks et al. 1996). We therefore designed an Ad2-based stuffer plasmid which contained a fragment of lambda DNA located within the E3 region as follows (FIG. 2B). pFG28, which contains the right 40 map units of Ad2(F. L. G., unpublished), was digested with PacI and ligated with PacI digested pCARPABS1 (Addison 1997), which contains a 5.6 kb fragment of lambda DNA (22346–27972 bp of the conventional lambda map) cloned into the unique BamHI site of pABS1 (Neo', Bett 1995). The resulting plasmid, pFG28CARP, was partially digested with HpaI, resulting in the loss of the neomycin resistance gene, part of the lambda DNA, and other bacterial sequences derived from pABS1, and recirculized, generating pFG28CARPc. To transfer the stuffer segment to Ad2LC8c, DNA isolated from Ad2LC8c virions was digested with SrfI and cotransfected with pFG28CARPc into 293 cells (FIG. 2B). The resulting viruses were screened by restriction analysis for those containing the lambda stuffer segment within the E3 region, and one positive isolate, designated Ad2LC8cCARP, was used for subsequent experiments.

Generation of Ad2-based Helper Virus

We have previously shown that hdAd can efficiently transduce cells in vitro and in vivo, and can lead to long term transgene expression with dramatically reduced cellular and inflammatory responses, compared to first generation Ad vectors (Schiedner et al. 1998, Morsy et al. 1998, Morral et al. 1998). Although the hdAd DNA does persist within non-dividing or slowly cycling cells for long times, the episomal nature of Ads (and hdAds) may mean that the vector DNA will eventually be lost from the cell. Thus, although hdAds allow for longer-tern transgene expression than observed with first generation Ads, there may be a requirement for repeat vector administration in order to "boost" transgene expression levels. The formation of neutralizing antibodies in immunized animals, which would occur due to the processing and presentation of virion proteins, would reduce the effectiveness of repeat administrations of hdAds, as found with first generation Ad vectors. Use of alternative Ad serotypes, either of the same (Mack et al. 1997, Roy et al. 1998, A. L. Beaudet, unpublished results) or different (Massrangeli et al. 1996, Kass-Eisler et al. 1996) subgroup, allows repeat first generation vector administration. We therefore undertook to (1) construct and characterize a helper virus based on a different serotype than our Ad5-based helper virus, and (2) determine if sequential use of vectors derived from different serotypes could permit efficient hdAd vector readministration.

Ad2LC8cCARP contains an Ad5left-end identical to that of our previous helper virus Ad5LC8cluc including the "floxed" packaging signal. We would therefore expect that the efficiency of Cre-mediated excision of the packaging signal ($\Psi$) would be similar for the two viruses. Experiments to test for excision in the 293Cre4 cell line showed that $\Psi$ was indeed excised from Ad2LC8cCARP with an efficiency similar to that observed for Ad5LC8cluc. Thus, Ad2LC8cCARP should act as an equally effective helper virus in our Cre/loxP system, resulting in only very low levels of helper virus contamination in the resulting vector stocks.

Ad2LC8cCARP encodes all structural proteins derived from Ad2, with the exception of pIX. The pIX gene is located immediately adjacent to E1, and encodes a minor virion structural component that has not been shown to be a major target for neutralizing antibody activity (Wohlfart 1988, Gahery-Segard et al. 1998), and is highly conserved between the two serotypes (138 of 139 amino acids are identical between Ad2and Ad5 pIX). Thus, the presence of an Ad5-pIX in our "Ad2" hdAd vectors should not interfere with their ability to transduce cells in the presence of anti-Ad5 antibodies. We also included a lent of lambda DNA within the E3 region of Ad2LC8cCARP as a stuffer to prevent RCA formation. Were Ad2LC8cCARP to recombine with the Ad5 sequences contained in the 293 or 293Cre4 cells, it would generate a virus of approximately 39 kb, which greatly exceeds the upper limit for Ad DNA packaging (Bett et al. 1993). Consequently, as with our earlier helper Ad5 LC8cluc, we have not observed RCA in our helper virus preparations or in stocks of vector produced using Ad2LC8cCARP.

Amplification of a hdAd Using Ad2LC8cCARP

To determine if Ad2LC8cCARP could amplify hdAd with an efficiency equal to that of Ad5LC8cluc, we transfected duplicate 60-mm dishes of 293Cre cells with 5 $\mu$g of pRP1050and, next day, infected the monolayers at an moi of 5 with Ad2LC8cCARP. After complete CPE (approximately 72 hr), the monolayers were harvested into the medium, freeze/thawed, and an aliquot of the lysates analyzed for lacZ-transducing particles. Ad2RP1050was rescued at a frequency of approximately 400 bfu per pmol of transfected DNA, which is similar to the efficiency previously observed for plasmids of comparable size using Ad5LC8cluc (Parks and Graham 1997), suggesting that Ad2LC8cCARP could indeed act as an effective helper virus in the 293Cre4 cells.

Figure 3:
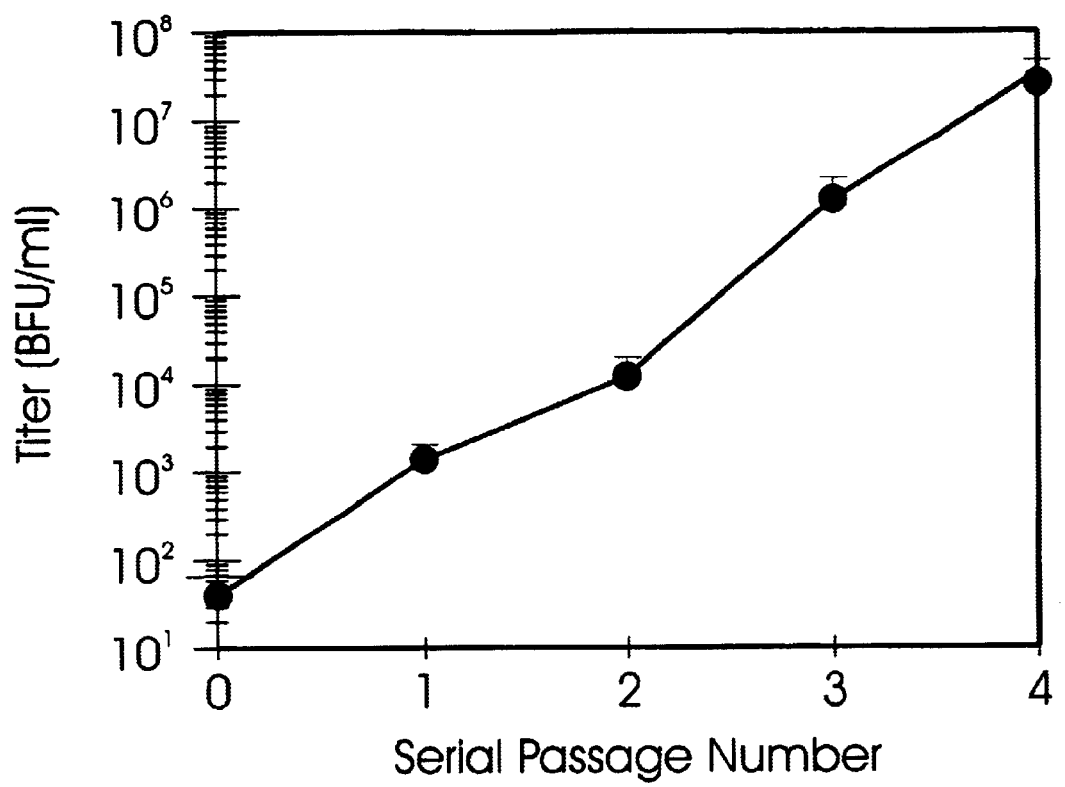
FIG. 3. Amplification of Ad2RP1050 using Ad2LC8cCARP. After each serial passage, an aliquot of the resulting crude vector lysates was titered for the presence of lacZ-transducing particles (blue formning units—bfu), as previously described (Parks et al. 1996). Amplifications were performed in duplicate, and the average bfu/ml is reported.

We then subjected an aliquot of the crude lysates (500 $\mu$l) to serial passage on Ad2LC8cCARP-infected 293Cre cells, in order to determine the kinetics of vector amplification. As shown in FIG. 3, Ad2RP1050was amplified using Ad2LC8cCARP at a rate similar to that previously observed for the Ad5LC8cluc helper virus (R. J. P. and F. L. G., unpublished results) and, after 4 serial passages on the helper virus-infected 293Cre cells, reached a titer of $3.4\times10^7$ bfu/ml. A large scale preparation of Ad2RP1050was performed, yielding $3\times10^{11}$ bfu from 20 150-mm dishes, with a helper virus contamination of $3.2\times10^7$ pfu/ml (~0.02% of the Ad2RP1050 titer). We conclude that Ad2LC8cCARP can act as a helper virus in 293Cre4 cells with an efficiency similar to that of Ad5 LC8cluc.

Effect of Ad5 Neutralizing Antibodies on hdAd2

Figure 4:
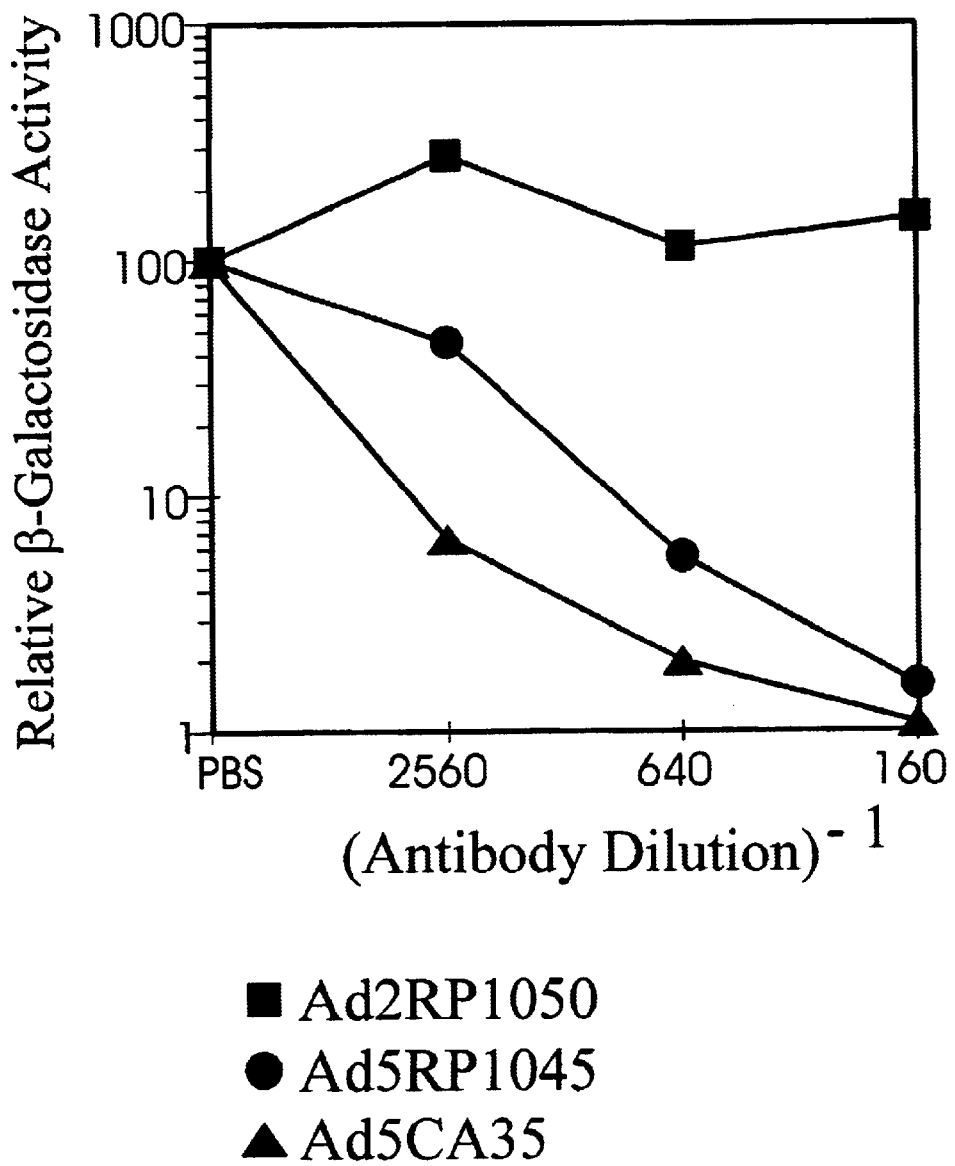
FIG. 4. Effect of Ad5neutralizing antibodies on hdAd2 or hdAd5. Serial dilutions of Ad5 neutralizing antibodies were incubated for 1 hr with $10^6$ bfu of Ad2RP1050 or Ad5 RP1045, or $10^6$ pfu of Ad5CA35, a first generation Ad vector containing an identical expression cassette in place of the E1 region (Addison et al. 1997). The resulting vector was used to infect 22-mm dishes of A549 cells, and the quantity of β-gal assayed at 24 hr post-transduction. Using this assay, the quantity of β-gal expressed is proportional to the transduction efficiency (ie titer) of the vector.

In theory, an hdAd based on an Ad2 serotype should not be affected by Ad5 neutralizing antibodies, allowing for vector readministration in animals previously treated with an Ad5-based hdAd. To determine if Ad2RP1050 was sensitive to antibodies generated against Ad5, $10^6$ bfu of Ad2RP1050, Ad5RP1045 or Ad5CA35 were incubated with serial dilutions of Ad5-neutralizing serum, and then used to infect A549 cells. Twenty-four hours later, crude cell extracts were prepared from the infected cells and assayed for $\beta$-gal activity. In this assay, infectivity directly correlates with $\beta$-gal activity and thus neutralization of the vector by antibody leads to a corresponding reduction in $\beta$-gal activity. Both Ad5CA35 and Ad5RP1045 were neutralized by incubation with the Ad5 antibodies, with an almost 100-fold decrease in $\beta$-gal activity at the highest antibody concentration (FIG. 4). In contrast, no decrease in $\beta$-gal activity (or virus infectivity) was noted for Ad2RP1050. These results indicate that the virion protein components derived from Ad2LC8cCARP and present in Ad2RP1050 are not sensitive to Ad5 neutralizing antibodies.

EXAMPLE 5

Transgene Expression Studies

Methods for preparation of cell samples and assays for $\beta$-gal are described elsewhere (Parks et al. submitted) and are known in the art. Assays for hSEAP activity were performed using a chemiluminescence kit, as described by the manufacturer (Tropix), with the exception that the serum samples were not heat treated prior to assay, resulting in a slightly higher background level of AP activity. For in vivo expression studies, adult female FVB/n mice (Harlan) were injected through the tail vein with $5\times10^{10}$ particles of vector in a volume of 200 $\mu$l. At various times post injection, blood samples were removed by orbital bleed, incubated overnight at 4° C., and the serum cleared by two rounds of centrifugation at 16,000 xg for 5 min in a microcentrifuge. The serum samples were stored at $-70$° C. until the end of the experiment. The method for preparation and analysis of $\beta$-gal levels in the liver of mice is well known.

In vitro Transgene Expression

Figure 5:
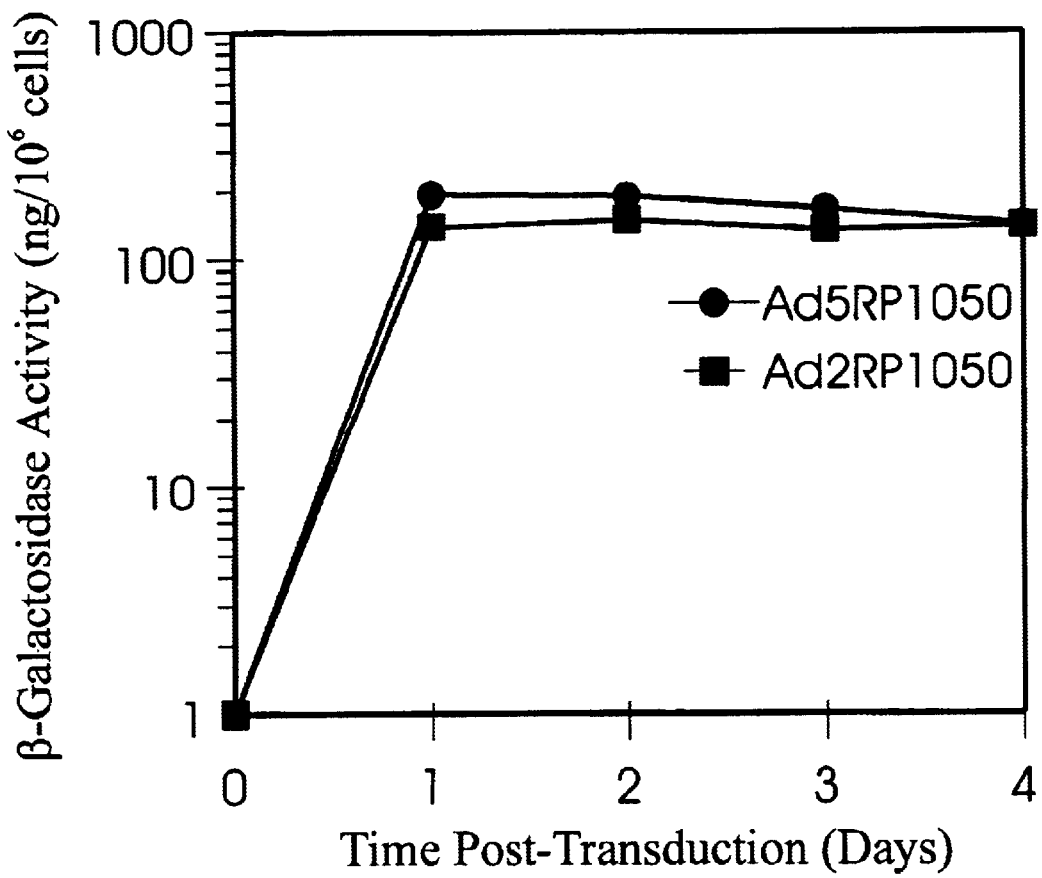
FIG. 5. In vitro expression from an Ad2- versus Ad5-based hdAd. Ad2RP1050 and Ad5 RP1045 are similar in structure, and contain an identical MCMV-lacZ expression cassette, but were generated using Ad2LC8cCARP and AdLC8cluc, respectively. Monolayers of A549 cells in 60-mm dishes were transduced in duplicate with $10^6$ bfu of vector, crude protein lysates prepared at various times post-transduction, and assayed for β-gal activity. The average of the duplicate samples is reported FIG. 6. In vivo expression from an hdAd2. Adult FVB/n mice were injected through the tail vein with $5\times10^{10}$ particles (approximately $5\times10^8$ transducing particles) of Ad2RP1046 (n=6). At various times post-injection, blood samples were removed by orbital bleed, and the serum isolated. Aliquots of serum were assayed for hSEAP activity using a chemiluminescent assay, and compared to a standard curve of purified hSEAP to determine the quantity of hSEAP in each sample. The average hSEAP for all mice is reported.

Although Ad2RP1050 and Ad5RP1050 are genetically identical, and would be predicted to have virtually identical expression characteristics, the efficiency of cell transduction could be affected by the presence of different virion capsid proteins. It is also possible that subtle differences in the protein coat or core proteins contained within the virion might influence the efficiency of transport of the hdAd DNA to the nucleus or affect promoter activity. We therefore examined transgene expression of Ad2RP1050 and Ad5 RP1050 in transduced A549 cells. We chose A549 since E1-deleted first generation vectors do not undergo productive infection in these cells, and our analysis of transgene expression over time would not be complicated by the presence of small quantities of helper virus. Monolayers of A549 cells in 60-mm dishes were transduced in duplicate with $10^6$ bfu of Ad2RP1050 or Ad5RP1050 and, at various times post-transduction, crude protein extracts were prepared and analyzed for $\beta$-gal activity. The hdAd2- and hdAd5-lacZ vectors had virtually identical expression characteristics in vitro over the duration of the experiment (FIG. 5). We conclude that hdAd generated using an Ad2- or Ad5-based helper virus have identical transduction efficiencies and transgene expression characteristics in vitro.

Transgene Expression in Vivo

Figure 6:
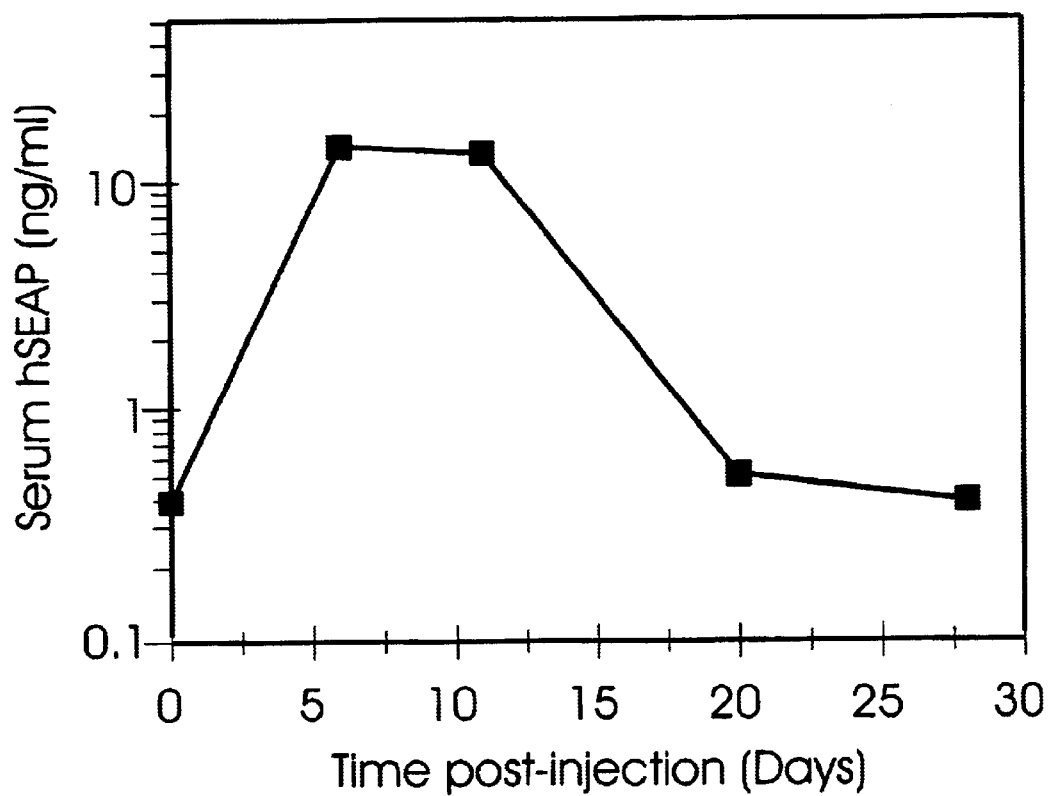

We next examined the ability of the hdAd2 to transduce mouse hepatic cells in vivo. We injected FVB/n mice through the tail vein with $5\times10^{10}$ particles of Ad2RP1046, and determined the level of hSEAP in the serum of animals at various times post-transduction. Injection of Ad vectors through the tail vein results in the majority of the vector being delivered to, and retained in, the liver resulting in high efficiency transduction of hepatocytes (Guo et al. 1996), and, for proteins efficiently secreted from the transduced cell, can lead to high levels of transgene products in the serum of treated animals (Morral et al. 1998, Morsy et al. 1998, Scheidner et al. 1998). As shown in FIG. 6, high levels of hSEAP were detected in the serum of transduced animals. Mice injected with a control Ad vector showed only a small increase in serum AP levels (approximately 3-fold above background, data not shown), presumably due to minor liver toxicity. Maximum levels of expression (approximately 14 ng per ml of serum) were obtained within one week of vector injection, remained constant for approximately 2 weeks, and declined to background levels within 3 weeks. The maximum level of protein expression is similar to that observed for a first generation Ad vector with an identical expression cassette (~10 ng per ml of serum, G. Maelandsmo, R. J. P. and F. L. G., unpublished results). The duration of hSEAP expression (~14 days) is consistent with that observed in other studies with a hdAd encoding a potentially immunogenic transgene (Parks et al. submitted). We conclude that hdAds generated using the Ad2 helper virus are able to efficiently transduce cells in vivo, and can lead to high levels of transgene expression, similar to Ad5-based hdAd.

EXAMPLE 6

Virus Neutralization Assays

Figure 7:
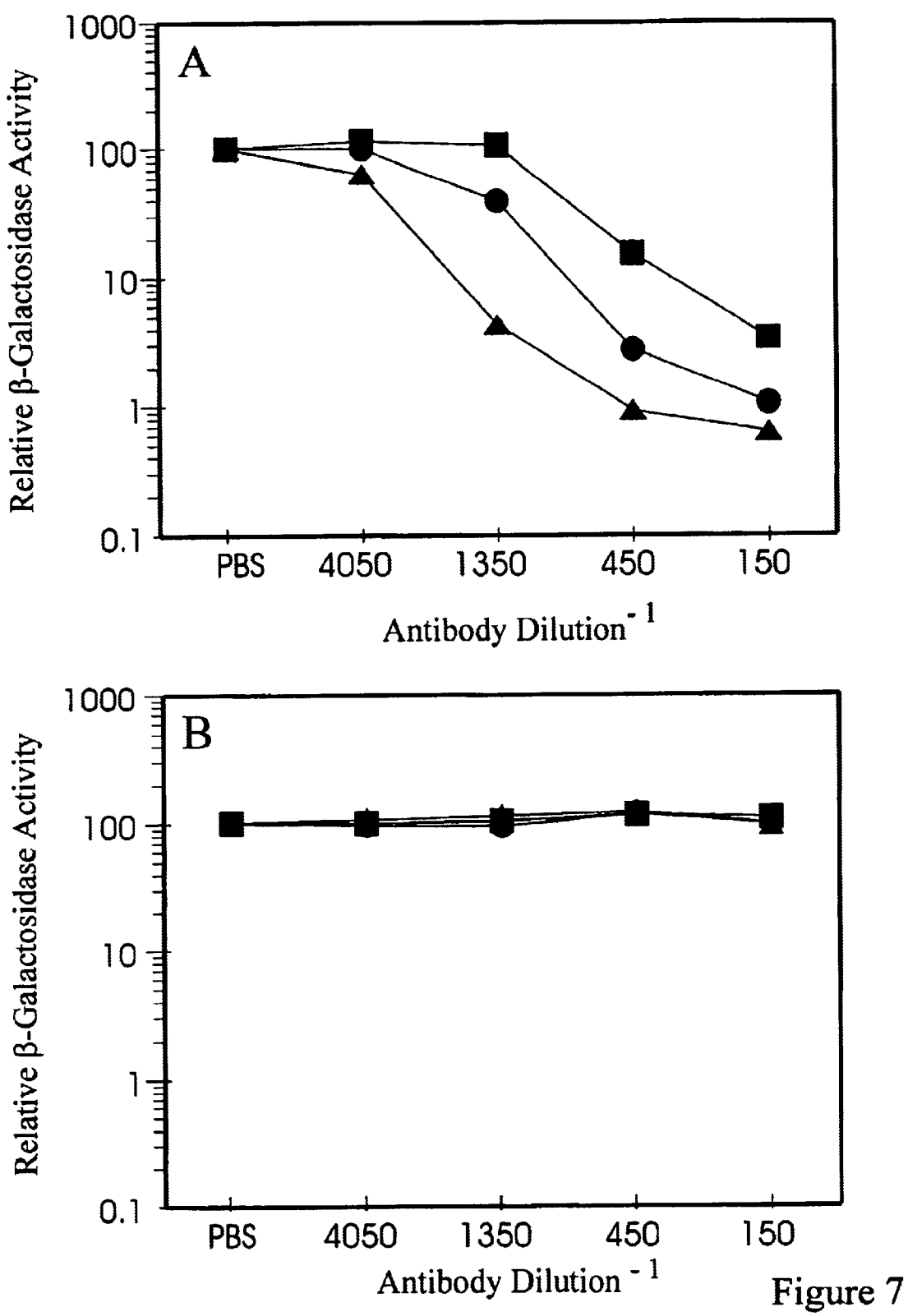
FIG. 7. Formation of Ad2-specific neutralizing antibodies in animals immunized with an hdAd2. Adult FVB/n mice (n=3) were injected through the tail vein with $5\times10^{10}$ particles of to Ad2RP1046. At Day 28 post-injection, serum samples were collected and assayed for Ad neutralizing antibodies, as described in the Materials and Methods. Serial dilutions of antibody were incubated with Ad2RP1050 (Panel A) or Ad5RP1050 (Panel B) for 1 hr, and assayed for transduction efficiency on A549 cells. The data from all 3 mice are presented.
Figure 8:
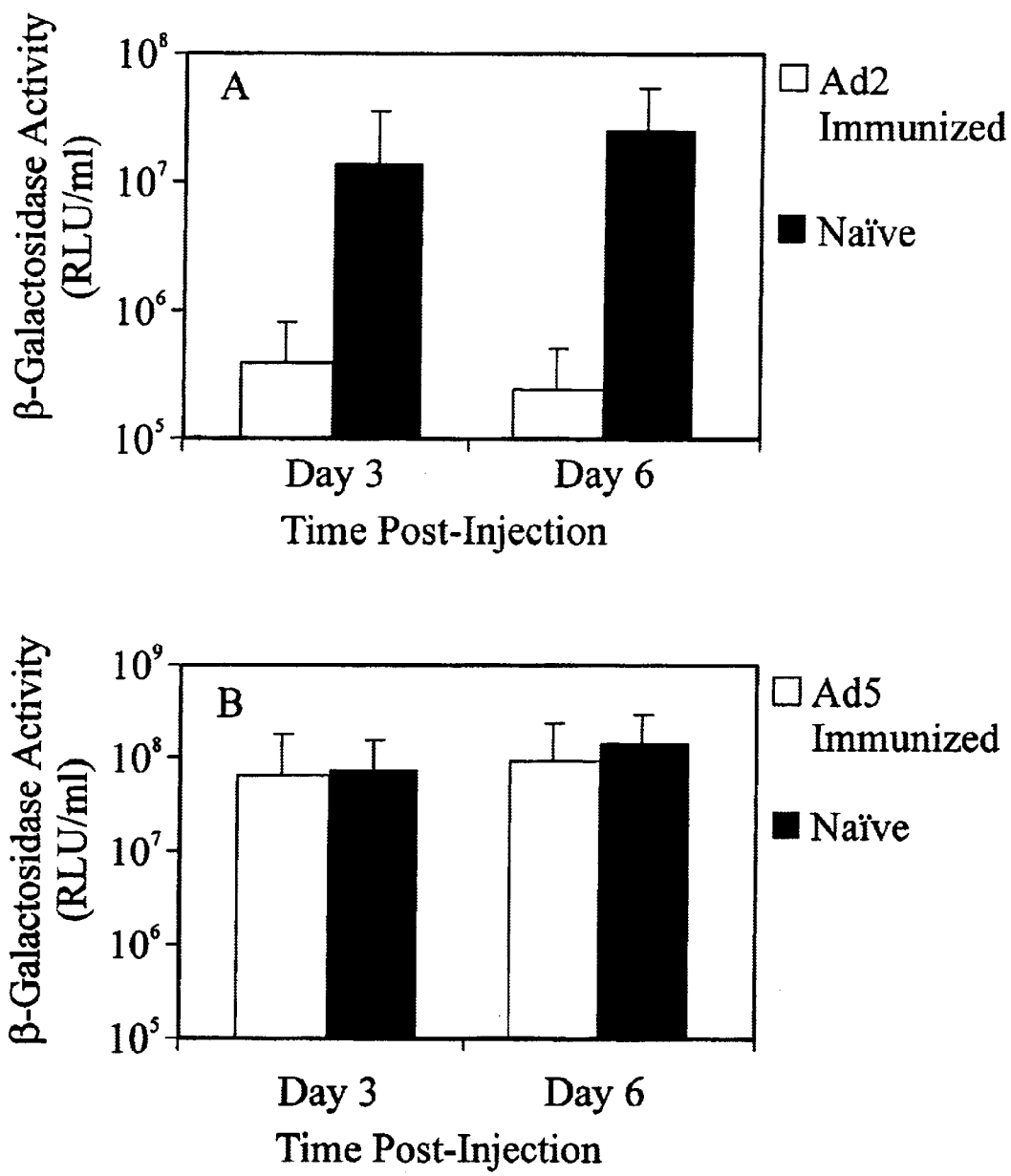
FIG. 8. Transgene expression from pre-immunized mice (hdAd2) using either the same (hdAd2) or alternative (hdAd5) serotype. FVB/n mice were immunized with $10^{10}$ particles of Ad2RP1046 and, 90 days later, injected i. v. with $10^3$ bfu of Ad2RP1050 or Ad5RP1050. Three or six days after the second vector was administered, the mice were sacrificed and the livers assayed for β-gal activity. Each bar represents the average of two mice, and the error bars represent the maximum value.

The Ad5 neutralizing antibodies used in these experiments were generated in rabbits by injection of a first-generation Ad5 vector (M. Anton and F. L. Graham, unpublished) and Ad2 antibodies were made in mice by injecting a serotype 2 hdAd. One skilled in the art would appreciate that neutralizing antibodies could also be generated in mice or rabbits or other animals by injection with wild type Ad2 or Ad5 viruses. Aliquots ($10^6$ bfu in 100 $\mu$l) of a first generation Ad vector (Ad5CA35, Addison et al. 1997), Ad5RP1045, AdRP1050, or Ad2RP1050, all containing an identical β-gal expression cassette, were incubated with serial dilutions (100 $\mu$l) of antibody-containing serum. After a 1 hr at 37° C., the treated vectors were used to infect 22 mm dishes of A549 cells for 1 h, the monolayers washed twice with PBS, maintenance medium replaced, and the quantity of β-gal present within the cells assayed 24 hr later. In this assay, the quantity of β-gal produced in the cells correlates directly with the efficiency of cell transduction.
Generation of Neutralizing Antibodies in hdAd2-immunized Animals We next wished to determine whether animals immunized with a hdAd2 would generate neutralizing antibodies to Ad2, and whether these antibodies would have any effect on a hdAd5. We therefore analysed serum collected at 28 days post-injection from mice injected i.v. with $5 \times 10^{10}$ particles of Ad2RP1046 for neutralizing antibodies to Ad2or Ad5. Serum samples were serially diluted and incubated with Ad2RP1050 or Ad5RP1050, and the resulting vector assayed for the ability to transduce A549 cells and express lacZ, as described above. All of the animals immunized with Ad2RP1046 produced neutralizing antibodies to Ad2, which resulted in a 30- to 100-fold decrease in Ad2RP1050 transduction at the highest antibody concentrations examined (FIG. 7). In contrast, there was no effect on Ad5RP1050, indicating that the hdAd2-immunized animals produced antibodies that were specific to Ad2. Therefore, it appears that helper-dependent Ad vectors based on alternative serotypes have the same general virion characteristics, with respect to presentation of surface antigens, as first generation Ad vectors. Based on these observations, we would predict that use of hdAd based on alternative Ad serotypes should permit vector readministration.
Use of hdAd of Alternative Serotype Allows for Repeat Vector Administration Since mice immunized with the hdAd2 generated antibodies to Ad2, and those antibodies did not cross-react with Ad5, we next determined whether subsequent delivery of hdAd5 to mice preimmunized with hdAd2 could overcome the effects of neutralizing antibodies against Ad2 and result in higher levels of transgene expression compared to read-ministration of hdAd2. Mice were immunized with $10^{10}$ particles of Ad2RP1046 and, 90 days later, injected with $10^8$ bfu of either Ad2RP1050 or Ad5RP1050. As a control, naive animals were injected in parallel with the same set of lacz-expressing vectors. At three and six days after administration of the lacZ vector, the animals were euthanized and the livers removed and assayed for β-gal activity. Administration of a serotype 2 vector into animals immunized against Ad2 resulted in an over 30-fold reduction in transgene expression ($4.0 \times 10^5$ versus $2.1 \times 10^7$ rlu per tissue) at day 3, and a 100-fold reduction ($2.5 \times 10^5$ versus $2.6 \times 10^7$ rlu per tissue) by day 6 post-injection compared to naive animals (FIG. 8A). In contrast, surprisingly, no decrease in transgene expression was observed relative to that in naive animals when the re-administered vector was of a different serotype (FIG. 8B). Interestingly, we did not observe a decrease in expression of lacZ between days 3 and 6 in the hdAd2-hdAd5 treatment, as has been observed for similar treatments using first generation Ad vectors (Mack et al. 1997). The decrease in expression observed by Mack et al. (1997) was attributed to cellular immune processes, and suggests that either hdAd do not elicit such destructive processes or, alternatively, are poor targets.

REFERENCES

Addison, C. L. 1997. Construction and characterization of adenovirus vectors expressing interleukin-2 or -4 for the immunotherapy of cancer. Ph.D. Thesis, McMaster University, Hamilton, Ontario, Canada.

Addison, C. L., M. Hitt, D. Kunsken, and F. L. Graham. 1997. Comparison of the human versus murine cytomegalovirus immediate early promoters for transgene expression by adenovirus vectors. J. Gen. Virol. 78:1653–1661.

Amalfitano, A., M. A. Hauser, H. Hu, D. Serra, C. R. Begy, and J. S. Chamberlain. 1998. Production and characterization of improved adenovirus vectors with E1, E2b, and E3 genes deleted. J. Virol. 72:926–933.

Bett, A. J. 1995. Construction and characterization of recombinant human adenovirus type 5 vectors. Ph.D. Thesis, McMaster University, Hamilton, Ontario, Canada.

Belt, A. J., L. Prevec, and F. L. Graham. 1993. Packaging capacity and stability of human adenovirus type 5 vectors. J. Virol. 67:5911–5921.

Bruder, J. T., T. Jie, D. L. McVey, and I. Kovesdi. 1997. Expression of gp19K increases the persistence of transgene expression from an adenovirus vector in the mouse lung and liver. J. Virol. 71:7623–7628.

Chen, L., M. Anton, F. L. Graham. 1996. Production and characterization of human 293 cell lines expressing the site-specific recombinase Cre. Somat. Cell. Mol. Genet. 22:477–488.

Chen, H. H., L. M. Mack, R. Kelly, M. Ontell, S. Kochanek, and P. R. Clemens. 1997. Persistence in muscle of an adenovirus vector that lacks all viral genes. Proc. Natl. Acad. Sci. USA. 94:1645–1650.

Christ, M., M. Lusky, F. Stoeckel, D. Dreyer, A. Dieterle, A.-I. Michou, A. Pavirani, and M. Mehtali. 1997. Gene therapy with recombinant adenovirus vectors: evaluation of the host immune responses. Imm. Lett. 57:19–25.

Dai, Y. E. M. Schwarz, D. Gu, W. W. Zhang, N. Sarvetnick, and I. M. Verma. 1995. Cellular and humoral immune responses to adenovirus vectors containing factor IX gene: tolerization of factor IX and vector antigens allows for long-term expression. Proc. Natl. Acad. Sci. USA 92:1401–1405.

Dedieu, J.-F., E. Vigne, C. Torrent, C. Jullien, I. Mahfouz, J.-M. Caillaud, N. Aubailly, C. Orsini, J.-M. Guillaume, P. Opolon, P. Delaere, M. Perricaudet, and P. Yeb. 1997. Long-term gene delivery into the livers of immunocompetent mice with E1/E4-defective adenoviruses. J. Virol. 71:4626–4637.

Dong, J.-Y., D. Wang, F. W. Van Ginkel, D. W. Pascual and R. A. Frizzel. 1996. Systemic analysis of repeated gene delivery into animal lungs with a recombinant adenovirus vector. Hum. Gene Ther. 7:319–331.

Engelhardt, J. F., X. Ye, B. Doranz, and J. M. Wilson. 1994. Ablation of E2A in recombinant adenoviruses improves transgene persistence and decreases inflammatory response in mouse liver. Proc. Natl. Acad. Sci. USA 91:6196–6200.

Fang, B., H. Wang, G. Gordon, D. A. Bellinger, M. S. Read, K. M. Brinkhous, S. L. C. Woo, and R. C. Eisensmith. 1996. Lack of persistence of E1 recombinant adenoviral vectors containing a temperature-sensitive E2A mutation in immunocompetent mice and hemophilia B dogs. Gene Ther. 3:217–222.

Fisher, K. J., H. Choi, J. Burda, S.-J. Chen, and J. M. Wilson. 1996. Recombinant adenovirus deleted of all viral genes for gene therapy of cystic fibrosis. Virol. 217:11–22.

Gahery-Segard, H., F. Farace, D. Godfrin, J. Gaston, R. Lengagne, T. Tursz, P. Boulanger, and J. G. Guillet. 1998. Immune response to recombinant capsid proteins of adenovirus in humans: antifiber and anti-penton base antibodies have a synergistic effect on neutralizing activity. J. Virol. 72:2388–2397.

Gao, G.-P., Y. Yang, and J. M. Wilson. 1996. Biology of adenovirus vectors with E1 and E4 deletions for liver-directed gene therapy. J. Virol. 70:8934–8943.

Gilgenkrantz, H., D. Duboc, V. Juillard, D. Couton, A. Pavirani, J. G. Guilet, P. Briand and A. Kahn. 1995. Transient expression of genes transduced In vivo into heart using first generation adenoviral vectors: role of the immune response. Hum Gene Ther. 6:1265–1274.

Goldman, M. J., L. A. Litzky, J. F. Engelhardt, and J. M. Wilson. 1995. Transfer of the CFTR gene to the lung of nonhuman primates with E1-deleted, E2a-defective recombinant adenoviruses: a preclinical toxicology study. Hum. Gene Ther. 6:839–851.

Graham, F. L., J. Smiley, W. C. Russel and R. Nairn. 1977. Characteristics of a human cell line transformed by DNA from human adenovirus type 5. J. Gen. Virol. 36:59–74.

Guo, Z. S., L. H. Wang, R. C. Eisensmith, S. L. C. Woo. 1996. Evaluation of promoter strength for hepatic gene transfer in vivo following adenovirus-mediated gene transfer. Gene Ther. 3:802–810.

Haeker, S. E., H. H. Stedman, R. J. Balice-Gordon, D. B. J. Smith, J. P. Greelish, M. A. Mitchel, A. Wells, H. L. Sweeney, and J. M. Wilson. 1996. In vivo expression of full length human dystrophin from adenoviral vectors deleted of all viral genes. Hum. Gene Ther. 7:1907–1914.

Hardy, S., M. Kitamura, T., Harris-Stansil. Y. Dai, and M. L. Phipps. 1997. Construction of adenovirus vectors through Cre-lox recombination. J. Virol. 71:1842–1849.

Hitt, M. M., R. J. Parks, and F. L. Graham. 1998. Structure and genetic organization of adenovims vectors. In The Development of Human Gene Therapy, T. Friedman (ed.), Cold Spring Harbor Press, Cold Spring Harbor pp 61–86.

Hitt, M. M., C. L. Addison, and F. L. Graham. 1997. Human adenovirus vectors for gene transfer into mammalian cells. In Advances in Pharmacology, Vol. 40, T. August et al. (Eds), Academic Press, San Diego. p.p.137–206.

Hitt, M., A. J. Bett, C. L. Addison, L. Prevec, and F. L. Graham. 1995. Techniques for human adenovirus vector construction and characterization. Methods in Molecular Genetics. 7:13–30.

Ilan, Y, G. Droguett, N. R. Chowdhury, Y. Li, K. Sengupta, N. R. Thummala, A. Davidson, J. R. Chowdhury, and M. S. Horwitz. 1997. Insertion of the adenoviral E3 region into a recombinant viral vector prevents antiviral humoral and cellular immune responses and permits long-term gene expression. Proc. Natl. Acad. Sci. USA 94:2587–2592.

Jooss, K., Y. Yang, and J. M. Wilson. 1996. Cyclophosphamide diminishes inflammation and prolongs transgene expression following delivery of adenoviral vectors to mouse and lung. Hum. Gene Ther. 7:1555–1566.

Kaplan, J. M., J. A. St. George, S. E. Pennington, L. D. Keyes, R. P. Johnson, S. C. Wadsworth, and A. E. Smith. 1996. Humoral and cellular immune responses of nonhuman primates to long-term repeated lung exposure to Ad2/CFTR-2. Gene Ther. 3:117–127.

Kaplan, J. M. and A. E. Smith. 1997. Transient immunosuppression with deoxyspergualin improves longevity of transgene expression and ability to readminister adenoviral vectors to the mouse lung. Hum. Gene. Ther. 8:1095–1104.

Kass-Eisler, A., L. Leinwand, J. Gall, B. Bloom, and E. Falck-Pedersen. 1996. Circumventing the immune response to adenovirus-mediated gene therapy. Gene Ther. 3:154–162.

Kochanek, S., P. R. Clemens, K. Mitani, H.-H. Chen, S. Chan, and C. T. Caskey. 1996. A new adenoviral vector: replacement of all viral coding sequences with 28 kb independently expressing both full-length dystrophin and β-galactosidase. Proc. Natl. Acad. Sci USA 93:5731–5736.

Kolls, J. K., D. Lei, G. Odum, S. Nelson, W. R. Summer, M. A. Gerber, and J. E. Shellito. 1996. Use of transient CD4 lymphocyte depletion to prolong transgene expression of E1 deleted adenoviral vectors. Hum. Gene Ther. 7:489–497.

Kumar-Singh, R. and J. S. Chamberlain. 1996. Encapsidated adenovirus minichromosomes allow delivery and expression of a 14 kb dystrophin cDNA to muscle cells. Hum. Mol. Genet. 5:913–921.

Kuzmin, A. I., M. J. Finegold, and R. C. Eisensmith. 1997. Macrophage depletion increases the safety, efficacy, and persistence of adenovirus-mediated gene transfer in vivo. Gene Ther. 4:309–316.

Lee, M. G., M. A. Abina, H. Haddada, and M. Perricaudet. 1995. The constitutive expression of the immunomodulatory gp 19k protein in E1-, E3–adenoviral vectors strongly reduces the host cytotoxic T cell response against the vector. Gene Ther. 2:256–262.

Lieber, A., C.-Y. He, I. Kirillova, and M. A. Kay. 1996. Recombinant adenoviruses with large deletions generated by Cre-mediated excision exhibit different biological properties compared with first-generation vectors in vitro and in Yivo. J. Virol. 70:8944–8960.

Lieber, A., C.-Y. He, L. Meuse, D. Schowalter, I. Kirillova, B. Winther, and M. A. Kay. 1997. The role of Kupffer cell activation and viral gene expression in early liver toxicity after infusion of recombinant adenovirus vectors. J. Virol. 71:8798–8807.

Lochmuller, H., B. J. Petrof, G. Pari, N. Larochelle, V. Dodelet, Q. Wang, C. Allen, S. Prescott, B. Massie, J. Nalbantoglu, and G. Karpati. 1996. Transient immunosuppression by FK506 permits a sustained high-level dystrophin minigene transfer to skeletal muscle of adult dystrophic (mdx) mice. Gene Ther. 3:706–716.

Lusky, M., M. Christ, K. Rittner, A. Dieterle, D. Dreyer, B. Mourot, H. Schultz, F. Stoeckel, A. Pavirani, and M. Mehtali. 1998. In vitro and in vivo biology of recombinant adenovirus vectors with E1, E1/E2a, or E1/E4 deleted. J. Virol. 72:2022–2032.

Mack, C. A., W.-R. Song, H. Carpenter, T. J. Wickham, I. Kovesdi, B. G. Harvey, C. J. Magovern, O. W. Isom, T. Rosengart, E. Falck-Pedersen, N. R. Hackett, R. G. Crystal, and A. Mastrangeli. 1997. Circumvention of anti-adenovirus neutralizing immunity by administration of an adenoviral vector of an alternative serotype. Hum. Gene. Ther. 8:99–109.

McCoy, R. D., B. L. Davidson, B. J. Roessler, G. B. Huffnagle, S. L. Janich, T. J. Laing, and R. H. Simon. 1995. Pulmonary inflammation induced by incomplete or inactivated adenoviral particles. Hum. Gene Ther. 6:1553–1560.

Michou, A. I., L. Santoro, M. Christ, V. Julliard, A. Pavirani, and M. Mehtali. 1997. Adenovirus-mediated gene transfer: influence of transgene, mouse strain, and type of immune response on persistence of transgene expression. Gene Ther. 4:473–482.

Mitani, K, F. L. Graham, C. T. Caskey, and S. Kochanek. 1995. Rescue, propagation, and partial purification of a helper virus dependent adenovirus vector. Proc. Natl. Acad. Sci. USA 92:3854–3858.

Morral, N., W. O'Neal, H. Zhou, C. Langston, and A. Beaudet. 1997. Immune responses to reporter proteins and high viral dose limit duration of expression with adenoviral vectors: comparison of E2 a wild type and E2 a deleted vectors. Hum. Gene Ther. 8:1275–1286.

Morral, N., R. J. Parks, H. Zhou, C. Langston, G. Schiedner, J. Quinones, F. L. Graham, S. Kochanek, and A. L. Beaudet. 1998. High doses of a helper-dependent adenoviral vector yield supraphysiological levels of $\alpha_1$-antitrypsin with negligible toxicity. Human Gene Therapy, 10: 2709–2716, 1998.

Morsy, M. A., M. C. Gu, S. Motzel, J. Zhao, Q. Su, H. Allen, L. Franlin, R. J. Parks, F. L. Graham, S. Kochanek., A. J. Bett, and C. T. Caskey. 1998. An adenoviral vector deleted for all viral coding sequences results in enhanced safety and extended expression of a leptin transgene. Proc. Natl. Acad. Sci. USA. 95:7866–7871.

Parks, R. J., J. L. Bramson, Y. Wan., C. L. Addison, and F. L. Graham. Effects of stuffer DNA and viral protein coding sequences on transgene expression from first generation and helper-dependent adenoviral vectors. Submitted.

Parks, R. J. and F. L. Graham. 1997. A helper-dependent system for adenovirus vector production helps define a lower limit for efficient DNA packaging. J. Virol. 71:3293–3298.

Parks, R. J., L. Chen, M. Anton, U. Sankar, M. A. Rudnicki, and F. L. Graham. 1996. A helper-dependent adenovirus vector system: removal of helper virus by Cre-mediated excision of the viral packaging signal. Proc. Natl. Acad. Sci. USA. 93:13565–13570.

Poller, W., S. Schneider-Rasp, U. Liebert, F. Merklein, P. Thalheimer, A. Haack, R. Schwaab, C. Schmitt, H. H. Brackmann. 1996. Stabilization of transgene expression by incorporation of E3 region genes into an adenoviral factor IX vector and by transient anti-CD4 treatment of the host. Gene Ther. 3:521–530.

Roy, S., P. S. Shirley, A. McClelland, and M. Kaleko. 1988. Circumvention of immunity to the adenovirus major coat protein hexon. J. Virol. 72:6875–6879.

Sawchuk, S. J., G. P. Boivin, L. E. Duwel, W. Ball, K. Bove, B. Trapnell, and R. Hirsch. 1996. Anti-T cell receptor monoclonal antibody prolongs transgene expression following adenovirus-mediated in vivo gene transfer to mouse synovium. Hum. Gene Ther. 7:499–506.

Scaria, A., J. A. St. George, R. J. Gregory, R. J. Noelle, S. C. Wadsworth, A. E. Smith, and J. M. Kaplan. 1997. Antibody to CD40 ligand inhibits both humoral and cellular responses to adenoviral vectors and facilitates repeated administration to mouse airway. Gene Ther. 4:611–617.

Scbiedner, G., N. Morral, R. J. Parks, Y. Wu, S. C. Koopmans, C. Langston, F. L. Graham, A. L Beaudet, and S. Kochanek. 1998. Genomic DNA transfer with a high-capacity adenovirus vector results in improved in vivo gene expression and decreased toxicity. Nat. Genet. 18:180–183.

Schowalter, D. B., J. C. Tubb, M. Liu, C. B. Wilson, and M. A. Kay. 1997. Heterologous expression of adenovirus E3-gp19K in an E1a-deleted adenovirus vector inhibits MHC I expression in vitro, but does not prolong transgene expression in vivo. Gene Ther. 4:351–360.

Schulick, A. H., G. Vassalli, P. F. Dunn, G. Dong, J. J. Rade, C. Zanarron, and D. A. Dichek. 1997. Established immunity precludes adenovirus-mediated gene transfer in rat carotid arteries. J. Clin. Invest. 99:209–219.

Smith, T. A., B. D. White, J. M. Gardner, M. Kaleko, and A. McClelland. 1996. Transient immunosuppression permits successful repetitive intravenous administration of an adenovirus vector. Gene Ther. 3:496–502.

St. George, J. A., S. E. Pennington, J. M. Kaplan, L. J. Kleine, A. E. Smith, and S. C. Wadsworth. 1996. Biological response of nonhuman primates to long-term repeated lung exposure to Ad2/CFTR-2. Gene Ther. 3:103–116.

Tripathy, S. K., H. B. Black, E. Goldwasser, and J. M. Leiden. 1996. Immune responses to transgene-encoded proteins limit the stability of gene expression after injection of replication defective adenovirus vectors. Nat. Med. 2:545–550.

Van Ginkel, F. W., J. R. McGhee, C. Liu, J. W. Simecka, M. Yamamoto, R. A. Frizzell, E. J. Sorcher, H. Kiyono, and D. W. Pascual. 1997. Adenoviral gene delivery elicits distinct pulmonary-associated T helper cell responses to the vector and to its transgene. J. Immunol. 159:685–693.

Vilquin, J.-T., B. Guerette, I. Kinoshita, B. Roy, M., Goulet, C., Gravel, R. Roy, and J. P. Tremblay. 1995. FK506 immunosuppression to control the immune reactions triggered by first-generation adenovirus-mediated gene transfer. Hun. Gene Ther. 6:1391–1401.

Wang, Q., G. Greenburg, D. Bunch, D. Farson, and M. H. Finer. 1996. Persistent transgene expression in mouse liver following In vivo gene transfer with a DE1/DE4 adenovirus vector. Gene Ther. 4:393–400.

Wohlfart, C. 1988. Neutralization of adenoviruses: kinetics, stoichiometry, and mechanisms. J. Virol. 62:2321–2328.

Wolff, G., S. Worgall, N. van Rooijen, W.-R. Song, B.-G. Harvey, and R. G. Crystal. 1997. Enhancement of in vivo adenovirus-mediated gene transfer and expression by prior depletion of tissue macrophages in the target organ. J. Virol. 71:624–629.

Yang, Y., Q. Su, and J. M. Wilson. 1996a. Role of viral antigens in destructive cellular immune responses to adenovirus vector-transduced cells in mouse lung. J. Virol. 70:7209–7212.

Yang, Y., K. U. Jooss, Q. Su, H. C. J. Ertl and J. M. Wilson. 1996b. immune responses to viral antigens versus transgene product in the elimination of recombinant adenovirus-infected hepatocytes in vivo. Gene Ther. 3:137–144.

Yang, Y., Q. Li, H. C. J. Ertl, and J. M. Wilson. 1995a Cellular and humoral immune responses to viral antigens create barriers to lung-directed gene therapy with recombinant adenoviruses. J. Virol. 69:2004–2015.

Yang, Y., Z. Xiang, H. C. J. Ertl, and J. M. Wilson. 1995b. Upregulation of class I major histocompatibility complex antigens by interferon-g is necessary for T-cell mediated elimination of recombinant adeovirus-infected hepatocytes in vivo. Proc. Natl. Acad. Sci. USA 92:7257–7261.

Yang, Y., K Greenough, and J. M. Wilson. 1996c. Transient immune blockage prevents formation of neutralizing antibody to recombinant adenovirus and allows repeated gene transfer to mouse liver. Gene Ther. 3:412–420.

Yang, Y., F. A. Nunes, K. Berencsi, E. E. Furth, E. Gonczol, and J. M. Wilson. 1994a. Cellular immunity to viral antigens limits E1-deleted adenoviruses for gene therapy. Proc. Natl. Acad. Sci. USA 91:4407–4411.

Yang, Y., F. A. Nunes, K. Berencsi, E. Gonezol, J. F. Engelhardt, and J. M. Wilson. 1994b. Inactivation of E2a in recombinant adenoviruses improves the prospect for gene therapy in cystic fibrosis. Nat. Genet. 7:362–369.

Zepeda, M, and J. M. Wilson. 1996. Neonatal cotton rats do not exhibit destructive immune responses to adenoviral vectors. Gene Ther. 3:973–979.

Zsengeller, Z. K., G. P. Boivin, S. S. Sawchuk, B. C. Trapnell, J. A. Whitsett, and R. Hirsch. 1997. Anti-T cell receptor antibody prolongs transgene expression and reduces lung inflammation after adenovirus-mediated gene transfer. Hum. Gene. Ther. 8:935–941.

What is claimed is:

1. An adenoviral vector gene delivery system comprising:
   (a) a helper dependent adenovirus vector, hdAd, comprising a genome lacking virion capsid protein coding sequences, hut encoding a gene and expression control sequences, the expression of which is desired in a recipient cell;
   (b) helper adenoviruses of different serotypes, each of which encodes proteins whose functions are required for, when introduced into a cell line, replication and packaging of said hdAd genome, and wherein each said helper adenovirus comprises a packaging signal flanked on either side by at least one lox site; and
   (c) said cell line, wherein Cre recombinase is expressed in said cell line, into which may be introduced said hdAd and first one of said helper adenoviruses having a first particular serotype, such that packaged hdAd having the first particular serotype results, and wherein introduction of said hdAd and a second one of said helper viruses having a second particular serotype into cells of said cell line results in a packaged hdAd having the second particular serotype.

2. The adenoviral vector gene delivery system of claim 1, wherein said helper adenoviruses of different serotypes are comprised of serotype 2 and serotype 5.

3. The adenoviral vector gene delivery system of claim 1 wherein, in a series of said packaged helper dependent adenoviruses, at least two helper adenoviruses are from one subgroup of adenoviruses.

4. A method of making a series of genetically identical adenoviral vectors wherein each member of said series has a different serotype, for delivering and expressing a desirable gene in a recipient of said series of genetically identical adenoviral vectors, which comprises:
   (a) making a series of helper adenoviruses of differing serotypes, each serotype of said series of adenoviruses encoding a different set of capsid proteins, wherein each said helper adenovirus of said series comprises a packaging signal flanked on either side by a lox site;
   (b) making a helper dependent adenovirus vector, hdAd, having a genome encoding said gene, an adenoviral packaging signal, the adenoviral left ITR and the adenoviral right ITR, and as much additional nucleic acid sequences as are necessary to ensure expression of said gene and packaging of said hdAd genome, but not encoding virion capsid proteins;
   (c) generating a first stock of said hdAd in vitro by co-introducing into a cell, in which Cre recombinase is expressed, said hdAd genome and a helper adenovirus of a first serotype wherein said stock comprises infectious particles comprising said hdAd genome and capsid proteins encoded by said helper adenovirus of said first serotype;
   (d) repeating step (c) as many times as desired using a helper adenovirus of a different serotype each time said step (c) is repeated, such that a series of infectious hdAd stocks are generated, with each said stock having said different set of capsid proteins based on said different serotype; and
   (e) recovering said infectious hdAd stocks having a capsid of different serotype to obtain said series of genetically identical adenoviral vectors.

5. A series of genetically identical adenoviral vectors wherein each member of said series has a different serotype produced according to the method of claim 4.

6. A kit comprising:
   (a) an hdAd vector encoding a gene under control of a transcriptional promoter within a genome comprising an adenoviral right ITR, and adenoviral left ITR, an an adenoviral packaging sequence; and
   (b) a series of helper adenoviruses of different serotype, wherein each said helper adenovirus of said series comprises a packaging signal flanked on either side by a lox site.

* * * * *

UNITED STATES PATENT AND TRADEMARK OFFICE
CERTIFICATE OF CORRECTION

PATENT NO. : 6,730,507 B1
DATED : May 4, 2004
INVENTOR(S) : Frank L. Graham and Robin Parks It is certified that error appears in the above-identified patent and that said Letters Patent is hereby corrected as shown below:

Title page,
Delete Item [63], Related U.S. Application Data

Column 1,
Delete lines 6-24

Signed and Sealed this

Eleventh Day of January, 2005

JON W. DUDAS
*Director of the United States Patent and Trademark Office*